United States Patent [19]

Momoda et al.

[11] Patent Number: 5,693,830
[45] Date of Patent: Dec. 2, 1997

[54] PROCESS FOR PREPARING THE SPIROPYRONE COMPOUNDS

[75] Inventors: Junji Momoda; Satoshi Imura; Takashi Kobayakawa, all of Tokuyama, Japan

[73] Assignee: Tokuyama Corporation, Tokuyama, Japan

[21] Appl. No.: 224,864

[22] Filed: Apr. 8, 1994

[51] Int. Cl.$^6$ ................... C07D 493/10; C07D 493/00
[52] U.S. Cl. ................................................ 549/330
[58] Field of Search ............................ 549/340, 330

[56] References Cited

U.S. PATENT DOCUMENTS 4,980,089  12/1990  Heller ................................. 252/586

FOREIGN PATENT DOCUMENTS 246114  11/1987  European Pat. Off. .
362771  4/1990   European Pat. Off. .
401958  12/1990  European Pat. Off. .

OTHER PUBLICATIONS

Chemical Abstracts vol. 117 (20) #701990f, Tanaka et al. (1992) "Photochromic spiropyran compounds and their manufacture".
Chemical Abstracts vol. 115 (1) #8577g, Tanaka et al (1990) "Preparation of photochromic spiroarylpyran compounds".
Chemical Abstracts, vol. 115(14) #146678s, Imura et al. (1991) "Fast–fading photochromic chromene compositions".
Chemical Abstracts vol. 114(5) 42796s, Melzig (1990) "Preparation of spiro–[adanantane–2,2'–pyrans and oxazines] as photochromic substances".

Primary Examiner—C. Warren Ivy
Assistant Examiner—Raymond Covington
Attorney, Agent, or Firm—Sherman and Shalloway

[57] ABSTRACT

Spiropyrone compounds represented by the general formula

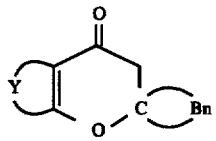

wherein

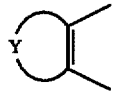

is a substituted or an unsubstituted aromatic hydrocarbon group or a substituted or an unsubstituted unsaturated heterocyclic group, and

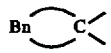

is a substituted or an unsubstituted 2-bicyclo[3,3,1]9-nonenylidene group, that are starting materials of spiropyran compounds which change from a colorless state into a colored or a densely colored state upon irradiation with the light containing ultraviolet rays such as the sunlight or the light of a mercury lamp, the change being reversible, and a process for preparing the spiropyrone compounds. The process comprises reacting a compound represented by the general formula

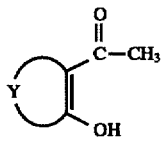

wherein

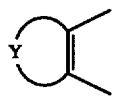

is as defined above, with a compound of the general formula

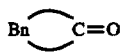

wherein

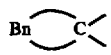

is as defined above.

32 Claims, 2 Drawing Sheets

PROCESS FOR PREPARING THE SPIROPYRONE COMPOUNDS

BACKGROUND OF THE INVENTION

1. Field of the Invention

The present invention relates to a process for preparing spiropyrone compounds. More specifically, the invention relates to a process for obtaining in good yields spiropyrone compounds that are starting materials of spiropyran compounds which change from a colorless state into a colored or a densely colored state upon irradiation with the light containing ultraviolet rays such as the sunlight or the light of a mercury lamp, the change being reversible, and maintaining excellent durability.

2. Prior Art

The photochromism is a phenomenon which has drawing attention in the past several years, and is a reversible action of a compound which quickly changes the color when it is irradiated with the light containing ultraviolet rays such as the sunlight or the light of a mercury lamp, and returns to the initial color when it is placed in a dark place without being irradiated with the light. The compounds having such properties are called photochromic compounds. A variety of compounds have heretofore been synthesized without, however, having any particular skeleton which is common in the structures thereof.

Japanese Laid-Open Patent Publication No. 11075/1991 discloses, as photochromic compounds, spiropyran compounds having a bicyclo[3,3,1]9-nonylidene group bonded to the second position of a benzopyran ring or the naphthopyran ring. These spiropyran compounds have execellent photochromic properties changing from a colorless state into a stale of developing yellow to orange color upon the irradiation with ultraviolet rays at normal temperature or in a temperature range slightly higher than the normal temperature (10° to 40° C.), returning from the colored state back to the colorless state within short periods of time, and exhibiting good color density. These spiropyran compounds are obtained by first obtaining, as a starting material, a spiropyrone compound in which a bicyclo[3,3,1]9-nonylidene group is bonded to the second position of a benzopyron ring or a naphthopyron ring by reacting a 1-acetyl-2-naphthol, a 1-acetyl-2-benzole or the like with a bicyclo[3,3,1]nonane-9-one or the like.

SUMMARY OF THE INVENTION

In the process for preparing the spiropyran compounds, however, the conversion for synthesizing the spiropyrone compounds is not so high that the desired spiropyran compounds are not obtained maintaining a satisfactory yield.

Under such circumstances, it has been desired to develop a process capable of obtaining in good yields spiropyrone compounds that serve as starting materials for preparing spiropyran compounds having excellent photochromic properties.

In view of the above-mentioned problems, the present inventors have conducted keen study, and have discovered the fact that the above problems could be solved by offering the structure in which a 2-bicyclo[3,3,1]9-nonenylidene group is bonded to the second position of a benzopyrone ring or the naphthopyrone ring of the spiropyrone compound, and have thus arrived at the present invention.

That is, the present invention is concerned with a process for preparing a spiropyrone compound represented by the following general formula (III),

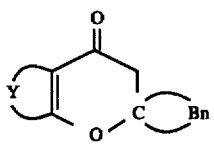

wherein

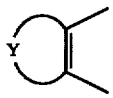

is a substituted or an unsubstituted aromatic hydrocarbon group or a substituted or an unsubstituted unsaturated heterocyclic group, and

is a substituted or an unsubstituted 2-bicyclo-[3,3,1]-9-nonenylidene group, comprising reacting a compound represented by the following general formula (I),

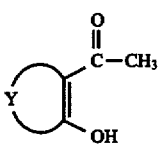

wherein

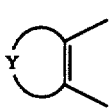

is as defined above, with a compound represented by the following general formula (II),

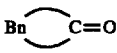

wherein

is as defined above.

DETAILED DESCRIPTION OF THE INVENTION

Figure 1:
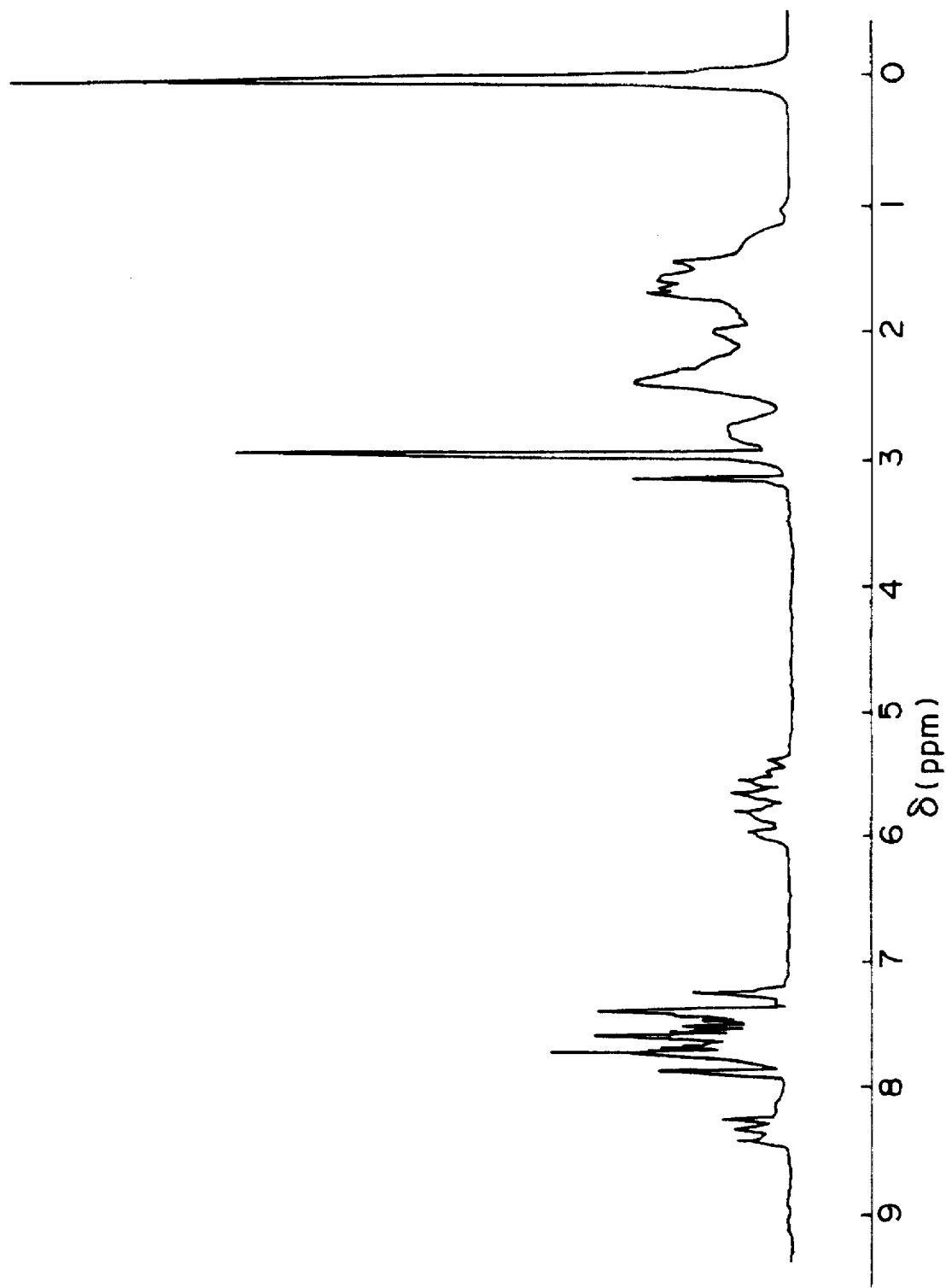
FIG. 1 is a chart of nuclear magnetic resonance spectra of protons of a spiropyrone compound obtained in Example 1.

When a compound represented by the above-mentioned general formula (I) is reacted with a compound represented by the above-mentioned general formula (II), the group

which is a 2-bicyclo[3,3,1,]9-nonenylidene group or a substituent thereof of the compound of the general formula (II) works to increase the reactivity. According to the present invention, therefore, it is made possible to obtain a spiropyrone compound represented by the above-mentioned general formula (III) maintaining a high yield.

According to the present invention, any known compound represented by the above-mentioned general formula (I) can be used without any limitation. In the compound of the above general formula (I), a group represented by

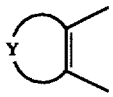

is a substituted or an unsubstituted aromatic hydrocarbon group or a substituted or an unsubstituted unsaturated heterocyclic group. A concrete example of the aromatic hydrocarbon group is a divalent group having 6 to 14 carbon atoms, and a divalent group derived from one benzene ring or a fused ring comprising 2 to 4 benzene rings is especially preferable. As examples of the ring constituting the aromatic hydrocarbon group, there can be mentioned a benzene ring, a naphthalene ring and a phenantherne ring. The aromatic hydrocarbon group may be substituted at least one member, or preferably, with 1 to 3 members. As example of aromatic hydrocarbon groups having substituents, there can be mentioned divalent groups derived from aromatic hydrocarbon rings such as toluene, xylene or the like substituted with an alkyl group having 1 to 4 carbon atoms such as a methyl group, an ethyl group or a t-butyl group. In addition to the above-mentioned substituents, there can be mentioned halogen atoms such as fluorine, chlorine, bromine and the like; a hydroxyl group; a cyano group; a nitro group; alkoxy groups having 1 to 4 carbon atoms such as a methoxy group, an ethoxy group and a tert-butoxy group; aryl groups having 6 to 10 carbon atoms such as a phenyl group and a tolyl group; substituted amino groups such as an alkylamino group having 1 to 4 carbon atoms like a methylamino group and an ethylamino group, and a dialkylamino group having 2 to 8 carbon atoms like a dimethylamino group and a diethylamino group; an alkyl group substituted with halogen having 1 to 2 carbon atoms such as a trifluoromethyl group; 5-membered and 6-membered monocyclic heterocyclic groups having 1 or 2 oxygen atoms, sulfur atoms or nitrogen atoms, such as a thienyl group, a furyl group or a pyrrolyl group. In the polysubstitution product substituted with these substituents, the substituents may be the same or different, and the positions of the substituents are changed depending upon the object and the application.

As the unsaturated heterocyclic group

there can be mentioned divalent group having 4 to 10 carbon atoms, and a 5- or 6-membered monocylic heterocyclic group containing one or two of nitrogen, oxygen and sulfur atoms, or a fused heterocyclic group formed by fusing a benzene ring to the above-mentioned monocyclic heterocyclic group. As the ring constituting the unsaturated heterocyclic group, there can be mentioned nitrogen-containing rings such as a pyridine ring, a quinoline ring and a pyrrole ring, oxygen-containing rings such as a furan ring and a benzofuran ring, and sulfur-containing rings such as a thiophone ring and a benzothiophene ring. According to the present invention, furthermore, it is allowable to use without any limitation the substituted and unsaturated heterocyclic groups in which the substituents described in relation to the above aromatic hydrocarbon groups are substituted for the above unsaturated heterocyclic rings.

According to the present invention, any known compound represented by the above-mentioned general formula (II) can be used without any limitation. In the compound of the general formula (II), the group

is a 2-bicyclo[3,3,1]9-nonenylidene group

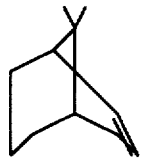

or a 2-bicyclo[3,3,1]9-nonenylidene group substituted with a substituent. Concrete examples of the substituent include halogen atoms such as fluorine, chlorine and bromine; a hydroxyl group; a cyano group; a nitro group a carboxyl group; alkyl groups having 1 to 4 carbon atoms such as a methyl group, an ethyl group and a t-butyl group; alkoxy groups having 1 to 4 carbon atoms such as a methoxy group, an ethoxy group and a tert-butoxy group; alkyl groups substituted with halogen having 1 or 2 carbon atoms such as a trifluoromethyl group and the like; aryl groups having 6 to 10 carbon atoms such as a phenyl group and a tolyl group; aryloxy groups having 6 to 10 carbon atoms such as a phenoxy group and a 1-naphthoxy group; aralkyl groups having 7 to 10 carbon atoms such as a benzyl group, a phenylethyl group and a phenylpropyl group; aralkoxy groups having 7 to 10 carbon atoms such as a benzyloxy group and the like; substituted amino groups such as an alkylamino group having 1 to 4 carbon atoms like a methylamino group and an ethylamino group, and a dialkylamino group having 2 to 8 carbon atoms like a dimethylamino group and diethylamino group; and alkoxycarbonyl groups having 2 to 10 carbon atoms such as an ethoxycarbonyl group and the like. These substituents are included not only as a one-substitution product but may also be included as a substitution product having two or more and, preferably, having 1 to 3 substituents. In the polysubstitution product, the substituents may be the same or different, and the positions of the substituents are changed depending upon the object and application.

According to the present invention, the reaction of the compound represented by the general formula (I) with the compound represented by the general formula (II) can be carried out under any condition without any particular limitation. Here, the reaction ratio of the mixture of these two compounds can be selected to lie over a wide range, and is usually selected to lie over a range of from 1:10 to 10:1 (molar ratio). The reaction temperature should usually be from 0° to 200° C., and the reaction time is usually selected to be from 1 to 20 hours. As a solvent for the above reaction, there can be used a polar non-protonic solvent such as an N-methylpyrolidone, a dimethylformamide, a toluene, a benzene, a tetrahydrofurane and the like.

The reaction is usually carried out in the presence of a condensing agent. Though there is no particular limitation, the condensing agent is generally a primary amine or a secondary amine. Concretely speaking, the primary amine or the secondary amine should be the one represented by the general formula,

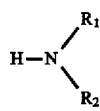

or

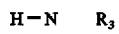

where either one of the groups $R_1$ and $R_2$ is a hydrogen atom and the other one is an alkyl group, or both of them are the same or different alkyl groups.

Though there is no particular limitation, the alkyl group should generally have 1 to 6 carbon atoms. Concrete examples include a methyl group, an ethyl group, a propyl group and a butyl group. Here, preferred examples of the primary amine include an N-ethylamine, an N-propylamine and the like. Furthermore, $R_3$ should be an alkylene group having 3 to 6 carbon atoms such as a tetramethylene group or a pentamethylene group; an oxyalkylene group having 3 to 6 carbon atoms such as

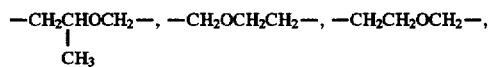

or $-CH_2O(CH_2)_3-$;

a thioalkylene group having 3 to 6 carbon atoms such as $-CH_2SCH_2CH_2-$, $-CH_2S(CH_2)_3-$, or $-CH_2CH_2SCH_2CH_2-$; or an azoalkylene group having 3 to 6 carbon atoms such as

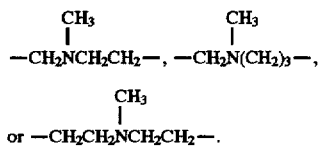

Here, preferred examples of the secondary amine include a diethylamine, a pyrrolydine, a piperidine, and a morpholine. The condensing agents should be used in an amount of, usually, from 0.1 to 10 moles per mole of the compound represented by the general formula (I).

The above-mentioned reaction is completed by removing the water formed during the reaction. The water can be removed either based on the azeotropy by using the Dien-Stark's device to remove the water out of the reaction system or by adding a dehydrating agent such as a calcium chloride, a calcium oxide or a zinc chloride to the reaction system to remove the water forming in the system.

Here, when the reaction of the compound represented by the general formula (I) with the compound represented by the general formula (II) is excessively continued in the presence of the primary amine or the secondary amine as the condensing agent, the spiropyrone compound represented by the general formula (III) that is once formed further reacts with the primary amine or the secondary amine, and a spiropyran compound represented by the following general formula (V) is gradually formed,

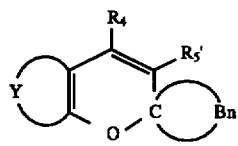

wherein

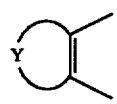

is a substituted or an unsubstituted aromatic hydrocarbon group or a substituted or an unsubstituted unsaturated heterocyclic group,

is a substituted or an unsubstituted 2-bicyclo[3,3,1]9-nonenylidene group, and either one of $R_4$ and $R_5'$ is a hydrogen atom and the other one is a group substituted amino group, spiropyran compound easily returns back to the spiropyrone compound represented by the general formula (III). In such a case, therefore, the reaction solution obtained by the reaction of the compound represented by the general formula (I) with the compound represented by the general formula (II) should be mixed with an aqueous solution of the acid, in order to return the above formed spiropyran compound back again to the spiropyrone compound represented by the general formula (III). In this case, though there is no particular limitation, the acid should usually be a mineral acid such as hydrochloric acid or sulfuric acid. Though there is no particular limitation, the acid is used in an amount equivalent to, or greater than, the amount of the condensing agent so that the reaction system becomes acidic. Water should be contained in an amount equal to, or greater than, the amount of the compound represented by the general formula (I) that is fed into the reaction solution. The aqueous solution of the acid may be added by preparing the aqueous solution of the acid in advance and mixing it into the reaction solution, or by separately mixing the acid and the water.

The spiropyrone compound represented by the general formula (III) obtained through the above-mentioned reaction can be separated and refined by any method but, usually, through the recrystallization.

The reaction of the compound represented by the general formula (I) with the compound represented by the general formula (II) forms the spiropyrone compound represented by the general formula (III),

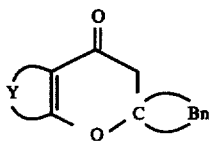

wherein

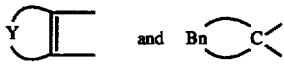

are the same as those of the general formula (I) and the general formula (II).

Representative examples of the spiropyrone compounds are as follows:

1) Spiro(2-bicyclo[3,3,1]nonene-9,2'-(2H)benzo(h)-4'-chromanone)
2) Spiro(2-bicyclo[3,3,1]nonene-9,2'-(2H)benzo(f)-4'-chromanone)
3) 8'-Cyanospiro(2-bicyclo[3,3,1]nonene-9,2'-2(H)-4'-chromanone)
4) 5'-Methoxy-7'-ethylspiro(2-bicyclo[3,3,1]nonene-9,2'-(2H)-4'-chromanone)
5) 5-Dimethylaminospiro(2-bicyclo[3,3,1]nonene-9,2'-(2H)benzo(f)-4'-chromanone)
6) 8-Methoxy-5'-chlorospiro(2-bicyclo[3,3,1]nonene-9,2'-(2H)benzo(f)-4'-chromanone)
7) Spiro(2-bicyclo[3,3,1]nonene-9,2'-(2H)isoquino(4,3-b)-4'-pyranone)
8) 5,8,8-Trimethylspiro(2-bicyclo[3,3,1]nonene-9,2'-(2H)pyrido(2,3-b)-4'-pyranone)
9) 7'-Phenyl-5-n-propylspiro(2-bicyclo[3,3,1]nonene-9,2'-2(H)benzo(h)-4'-chromanone)
10) 7'-Phenyl-5-chlorospiro(2-bicyclo[3,3,1]nonene-9,2'-(2H)-4'-chromanone)
11) Spiro(2-bicyclo[3,3,1]nonene-9,2'-(2H)pyrido(3,2-f)-4'-chromanone)
12) 5,7,7-Trimethylspiro(2-bicyclo[3,3,1]nonene9,2'-(2H)dibenzo(f,h)-4'-chromanone)
13) 7'-Nitro-10'-ethoxy-5,7,7-trimethylspiro(2-bicyclo[3,3,1]nonene-9,2'-(2H)benzo(h)-4'-chromanone)
14) 7'-Trifluoromethyl-10'-n-pentyl-5,7,7-trimethylspiro(2-bicyclo[3,3,1]nonene-9,2'-(2H)benzo(h)-4'-chromanone)
15) 5,10'-Diphenylspiro(2-bicyclo[3,3,1]nonene-9,2'-(2H)benzo(f)-4'-chromanone)
16) 7'-Thienylspiro(2-bicyclo[3,3,1]nonene-9,2'-(2H)benzo(h)-4'-chromanone)
17) 5-Trifluoromethyl-10'-n-propoxyspiro(2-bicyclo[3,3,1]-9,2'-(2H)pyrido(2,3-h)-4'-chromanone)
18) 5-Cyano-7'-furanylspiro(2-bicyclo[3,3,1]nonene-9,2'-(2H)benzo(h)-4'-chromanone)
19) 5-Benzyl-7'-dimethylaminospiro(2-bicyclo[3,3,1]nonene-9,2'-(2H)benzo-4'-chromanone)
20) 5-n Butyl 7-fluoro-6'-bromo-8'-hydroxyspiro(2-bicyclo[3,3,1]nonene-9,2'-(2H)benzo(f)-4'-chromanone)
21) 5-Ethyl-1-ethoxyspiro(2-bicyclo[3,3,1]nonene-9,2'-(2H)(benzo(b)thieno(2,3-b)-4'-pyranone)
22) Spiro(2-bicyclo[3,3,1]nonene-9,2'-(2H)methylpyrrolo(2,3-b)-4'-pyranone)
23) 5-Chlorospiro(2-bicyclo[3,3,1]nonene-9,2'-(2H)quino(3,4-b)-4'-pyranone)
24) 7-Bromospiro(2-bicyclo[3,3,1]nonene-9,2'-(2H)fluoro(2,3-b)-4'-pyranone)
25) 5'-Bromospiro(2-bicyclo[3,3,1]nonene-9,2'-2(H)thieno(2,3-b)-4'-pyranone)

The spiropyrone compounds obtained according to the present invention generally exist in the form of colorless and viscous liquids at normal temperature under normal pressure, and can be confirmed by means described in (a) to (c) below.

(a) The kind and number of protons existing in the molecules can be learned by the nuclear magnetic resonance spectrum of protons ($H^1$-NMR). That is, a peak appears near δ7 to 8.5 ppm due to aromatic protons, and broad peaks appear near δ1.2 to 3.5 ppm and near 5.3 to 5.7 ppm due no protons of a 2-bicyclo[3,3,1]9-nonenylidene group and protons at the third position of a spiropyrone ring. Further, the number of protons in the bonding group can be learned by comparing their δ peak intensities.

(b) Amounts in percent by weight of carbon, hydrogen, nitrogen, sulfur and halogen can be found by the elemental analysis. The amount in percent by weight of oxygen can be calculated by subtracting the sum of amounts in percent by weight of the above-found elements from 100. Therefore, the composition of the formed product can be determined.

(c) The kind of carbon present in the molecules can be learned by the 13C-nuclear magnetic resonance spectrum ($^{13}C$-NMR). Peaks appear near δ27 to 52 ppm due to carbon of the 2-bicyclo[3,3,1]9-nonenylidene group and carbon at the third position of the spiropyrone ring, and a peak appears near δ110 to 150 ppm due to carbon of an aromatic hydrocarbon group or an unsaturated heterocyclic group.

Next, the spiropyrone compound obtained by the above-mentioned process can be transformed into a spiropyran compound having good photochromic properties by changing the α-pyrone ring into a γ-pyran. The spiropyran compound should concretely be the one represented by the following general formula (IV)

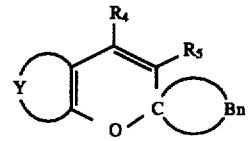

wherein

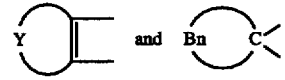

are the same as those of the aforementioned general formulas (I) and (II), and $R_4$ and $R_5$ are the same or different hydrogen atoms, alkyl groups, aralkyl groups, aryl groups or substituted amino groups, respectively, and when either one of $R_4$ and $R_5$ is a substituted amino group, the other one is a hydrogen atom.

In the above-mentioned spiropyran compound, though there is no particular limitation, the alkyl group should generally be the one having 1 to 20 carbon atoms and, preferably, 1 to 6 carbon atoms. The aralkyl group and the alkyl group should generally have 1 to 10 carbon atoms and, preferably, 1 to 4 carbon atoms. Concrete examples of the alkyl group and the aralkyl group include a methyl group, an ethyl group, a propyl group, a butyl group, a benzyl group, a phenylethyl group, a phenylpropyl group and a phenylbutyl group. The aryl group should have 6 to 10 carbon atoms. Preferred examples thereof include a phenyl group, a tolyl group, a xylyl group and a naphthyl group.

Furthermore, the substituted amino groups represented by $R_4$ and $R_5$ in the above general formula (IV) are the ones represented by the general formula

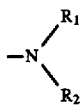

wherein $R_1$ and $R_2$ are as defined above, or

wherein $R_3$ is as defined above, which are residual groups remaining after hydrogen atoms are removed from the primary amine or the secondary amine used as the condensing agent.

According to the present invention, representative examples of the spiropyran compound represented by the above general formula (IV) are as follows:

1) Spiro 2-bicyclo(3,3,1)nonene-9,2'-(2H)benzo(h)chromene)
2) Spiro 2-bicyclo(3,3,1)nonene-9,2'-(2H)benzo(f)chromene)
3) 4'-Methylspiro(2-bicyclo(3,3,1,)nonene-9,2'-(2H)benzo(f)chromene)
4) 4'-Morpholinospiro(2-bicyclo[3,3,1]nonene-9,2'-(2H)benzo(f)chromene
5) 3'-Methylspiro(2-bicyclo[3,3,1]nonene-9,2'-(2H)benzo(f)chromene)
6) 3',4'-Dimethylspiro(2-bicyclo[3,3,1]nonene-9,2'-(2H)benzo(f)chromene)
7) 8'-Cyano-4'-pyrrolidinospiro(2-bicyclo(3,3,1)nonene-9,2'-(2H)benzochromene)
8) 7'-Ethyl-5'-methoxy-4'-morpholinospiro(2-bicyclo(3,3,1)nonene-9,2'-(2H)benzochromene)
9) 4'-Diethylamino-5-dimethylaminospiro(2-bicyclo(3,3,1)nonene-9,2'-(2H)benzo(f)chromene)
10) 5'-Chloro-4'-(1,3-thiazolidino)-7-methoxyspiro(2-bicyclo(3,3,1)nonene-9,2'-(2H)benzo(f)chromene)
11) 4'-(4-Methylpiperazino)spiro(2-bicyclo(3,3,1)nonene-9,2'-(2H)isoquino(4,3-b)pyran)
12) 5,8,8-Trimethylspiro(2-bicyclo(3,3,1)nonene-9,2'-(2H)pyrido(2,3-b)pyran)
13) 8'-Cyanospiro(2-bicyclo(3,3,1)nonene-9,2'-(2H)chromene)
14) 7'-Phenyl-5-n-propylspiro(2-bicyclo(3,3,1)nonene-9,2'-(2H)benzo(h)chromene)
15) 7'-Phenyl-5-chlorospiro(2-bicyclo(3,3,1)nonone-9,2'-(2H)chromene)
16) Spiro(2-bicyclo(3,3,1)nonone-9,2'-(2H)pyrido(3,2-f)chromene)
17) 5,7,7-trimethylspiro(2-bicyclo(3,3,1)nonone-9,2'-(2H)dibenzo(f,h)chromene)
18) 10'-Ethoxy-5,7,7-trimethyl-7'-nitrospiro(2-bicyclo(3,3,1)nonone-9,2'-(2H)benzo(h)chromene)
19) 5,7,7-Trimethyl-7'-trifluoromethyl-10'-n-pentylspiro(2-bicyclo(3,3,1)nonene-9,2'-(2H)benzo(h)chromene)
20) 5,10'-diphenylspiro(2-bicyclo(3,3,1)nonene-9,2'-(2H)benzo(f)chromene)
21) 7-Thienylspiro(2-bicyclo(3,3,1)nonene-9,2'-(2H)thienylbenzo(h)chromene)
22) 5-Trifluoromethyl-10'-n-propoxyspiro(2-bicyclo(3,3,1)nonene-9,2'-(2H)pyrido(2,3-h)chromene)
23) 5-Cyano-7'-furanylspiro(2-bicyclo(3,3,1)nonene-9,2'-(2H)(benzo(h))chromene)
24) 5-Butyl-7-fluoro-6'-bromo-8'-hydroxyspiro(2-bicyclo(3,3,1)nonene-9,2'-(2H)benzo(f)chromene)
25) 7'-Dimethylamino-5-benzylspiro(2-bicyclo(3,3,1)nonene-9,2'-(2H)benzo(h)chromene)
26) 5-Ethyl-8-ethoxyspiro(2-bicyclo(3,3,1)nonene-9,2'-(2H)(benzo(b)thieno(2,3-b)pyran)
27) Spiro(2-bicyclo(3,3,1)nonene-9,2'-(2H)methylpyrrolo(2,3-b)pyran)
28) 5-Chloro-4'-benzylspiro(2-bicyclo(3,3,1)nonene-9,2'-(2H)quino(3,4-b)pyran)
29) 8'-Cyano-4'-n-butylspiro(2-bicyclo(3,3,1)nonene-9,2'-(2H)chromene)
30) 4'-Phenyl-5,8,8-trimethylspiro(2-bicyclo(3,3,1)nonene-9,2'-(2H)pyrido(2,3-b)pyran
31) 7'-Phenyl-4'-ethyl-5-n-propylspiro(2-bicyclo[3,3,1]nonene-9,2'-(2H)benzo(h)chromene)
32) 4'-n-Butylspiro(2-bicyclo[3,3,1]nonene-9,2'-(2H)benzo(h)chromene)
33) 3'-n-Propylspiro(2-bicyclo[3,3,1]nonene-9,2'-(2H)benzo(f)chromene)
34) 3'-Benzylmethylspiro(2-bicyclo[3,3,1]nonene-9,2'-(2H)benzo(f)chromene)
35) 3'-i-Propylspiro(2-bicyclo[3,3,1]nonene-9,2'-(2H)benzo(f)chromene)
36) 3'-p-methoxyphenylspiro(2-bicyclo[3,3,1]nonene-9,2'-(2H)benzo(f)chromene)
37) 3'-Ethylspiro(2-bicyclo[3,3,1]nonene-9,2'-(2H)quino(3,4-b)pyran)
38) 3',4'-Dimethylspiro(2-bicyclo[3,3,1]nonene-9,2'-(2H)fluoro(2,3-b)pyran)
39) 4'-Ethyl-3'-benzyl-5'-bromospiro(2-bicyclo[3,3,1]nonene-9,2'-(2H)thieno(2,3-b)pyran)
40) 3'-n-Propyl-4'-benzylspiro(2-bicyclo[3,3,1]nonene-9,2'-(2H)benzo(f)chromene)
41) 3'-Benzylmethyl-4'-phenylspiro(2-bicyclo[3,3,1]nonene- 9,2'-(2H)benzo(f)chromene)
42) 3',4'-Diethylspiro(2-bicyclo[3,3,1]nonene-9,2'-(2H)benzo(h)chromene)

Though there is no particular limitation in the process for preparing the spiropyran compound represented by the general formula (IV) from the spiropyrone compound represented by the general formula (III) which is the starting material obtained by the present invention, there can be exemplified the following process. For instance, a compound of the general formula (IV) in which either one of $R_4$ and $R_5$ is a hydrogen atom and the other one is a substituted amino group, i.e., a compound of the following general formula (V),

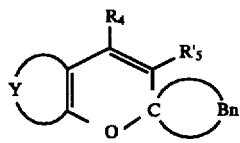

wherein

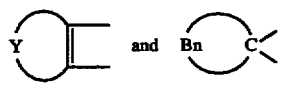

are the same as those of the above-mentioned general formulas (I) and (II), and either one of $R_4$ and $R_5'$ is a hydrogen atom and the other one is a group substituted amino group, is obtained by reacting the spiropyrone compound obtained by the present invention with the primary amine or the secondary amine of the formula

R—H wherein R is a substituted amino group which is the condensing agent used for the reaction of the compound of the general formula (I) with the compound of the general formula (II) under the same conditions as those of the above reaction. In this case, the primary amine or the secondary amine should be used in an amount of usually from 0.1 to 10 moles per mole of the spiropyrone compound. This process is usually carried out by executing the process of reacting the compound of the general formula (I) with the compound of the general formula (II) of the present invention in the presence of the primary amine or the secondary amine and, further, continuing the reaction by adding the above amine to the reaction solution. The reaction for obtaining the compound of the general formula (V) should be carried out for 5 to 20 hours as counted from the start of the reaction of the compound of the general formula (I) with the compound of the general formula (II).

A compound of the general formula (IV) in which $R_4$ and $R_5$ are both hydrogen atoms, i.e., a compound of the following general formula (VI)

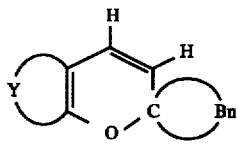

wherein

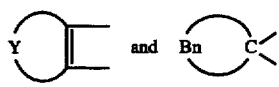

are the same as those of the above-mentioned general formulas (I) and (II), is obtained by, first, reducing the spiropyrone compound obtained by the present invention with a reducing agent to obtain a compound represented by the following general formula

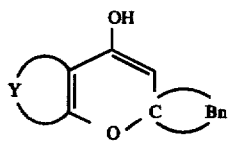

wherein

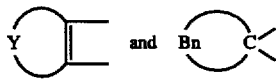

are the same as those of the above-mentioned general formulas (I) and (II), and, then, dehydrating this compound. Though there is no particular limitation, there is usually used, as the reducing agent, a hydrogen compound such as a sodium boron hydride or an aluminum lithium hydride. The reducing agent should be used in an amount of usually from 1 to 10 moles per a mole of the spiropyrone compound. The reaction temperature of the reducing reaction should be usually from 50° to 100° C. and the reaction time is usually selected to be from 1 to 10 hours. Though there is no particular limitation in the reaction solvent, it is desired to use a polar solvent such as a methanol, an ethanol, a tetrahydrofurane or a dimethylformamide. The dehydration may be carried out by any method. Usually, however, the dehydration is carried out by separating the product after the reduction reaction has been finished and then adding a dehydrating agent thereto. Here, though there is no particular limitation, there is usually used, as the dehydrating agent, anhydrous copper sulfate, hydrochloric acid, magnesium sulfate or alumina. The dehydrating agent should be used in an amount of usually from 0.1 to 10 parts by weight per a part by weight of the spiropyrone compound. The reaction temperature of the dehydration reaction should usually be from 50° to 200° C., and the reaction time is usually selected to be from 0.1 to 10 hours.

A compound of the general formula (IV) in which $R_4$ is an alkyl group, an aralkyl group or an aryl group, and $R_5$ is a hydrogen atom, i.e., a compound of the following general formula (VII)

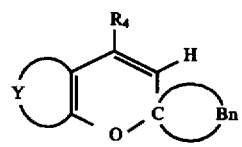

wherein

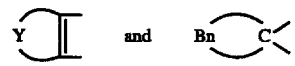

are the same as those of the above-mentioned general formulas (I) and (II), and $R_4$ is an alkyl group an aralkyl group or an aryl group, is obtained by, first, obtaining a compound of the following general formula

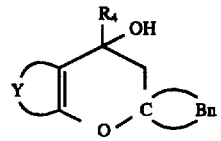

wherein

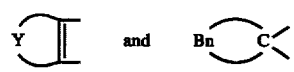

are the same as those of the above-mentioned general formulas (I) and (II), and $R_4$ is an alkyl group, an aralkyl group or an aryl group, by reacting the spiropyrone compound obtained by the present invention with a compound of the formula

or

wherein R is an alkyl group, an aryl group or an aralkyl group, and X is a halogen atom, and then dehydrating this compound. Here, as halogen For $R_4$—MgX, there should preferably be used bromine, chlorine or iodine. The organometal compound should be used usually in an amount of from 1 to 10 moles per a mole of the spiropyrone compound. The reaction temperature is usually from −20° to 70° C., and the reaction time is usually from 0.1 to 10 hours. As the solvent of the reaction, it is desired to use ethers such as an ethyl ether, a tetrahydrofurane or a dioxane. The compound obtained by the above reaction should be dehydrated by the same method as the one for obtaining the compound of the above-mentioned general formula (VI).

Furthermore a compound represented by the general formula (IV) wherein $R_4$ is a hydrogen atom and $R_5$ is an alkyl group, an aralkyl group or an aryl group, i.g., a compound of the following general formula (VIII)

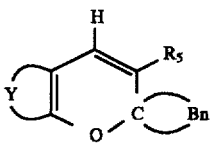

wherein

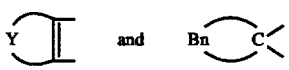

are the same as those of the above-mentioned general formulas (I) and (II), and $R_5$ is an alkyl group, an aralkyl group or an aryl group, is obtained by, first, carrying out the process for preparing the spiropyran compound represented by the above-mentioned general formula (V), reacting the spiropyran compounds of the general formula (V) with a compound of the formula $R_5X$ wherein $R_5$ is as defined above, to obtain a compound represented by the following general formula (IX)

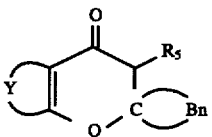

wherein

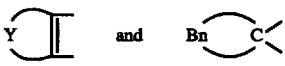

are the same as those of the above-mentioned general formulas (I) and (II), and $R_5$ is an alkyl group an aralkyl group or an aryl group, and reducing the thus obtained compound followed by dehydration. Here, iodine, bromine or chlorine is usually used as halogen for the compound of the formula $R_5X$. These halogen compounds should be used usually in an amount of 1 to 10 moles per a mole of the spiropyrone compound. The reaction temperature for obtaining the compound represented by the general formula (IX) should desirably be from −20° to 50° C., and the reaction time is usually from 0.1 to 10 hours. Though there is no particular limitation, desired examples of the solvent of the reaction are polar solvents such as a methanol, an ethanol, a toluene and a tetrahydrofurane. The compound represented by the general formula (IX) is reduced with a reducing agent and is then dehydrated in the same manner as the one carried out for obtaining the compound represented by the above-mentioned general formula (VI).

Furthermore, a compound represented by the general formula (IV) wherein $R_4$ and $R_5$ are the same or different alkyl groups, aralkyl groups or aryl groups, i.e., a compound represented by the following general formula (X)

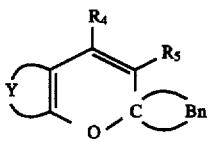

wherein

are the same as those of the above-mentioned general formulas (I) and (II), and $R_4$ and $R_5$ are the same or different alkyl groups, aralkyl groups or aryl groups, is obtained by, first, obtaining a compound of the following general formula

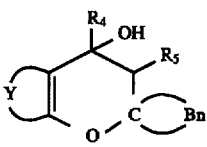

wherein

are the same as those of the above-mentioned general formulas (I) and (II), and $R_4$ $R_5$ are the same or different alkyl groups, aralkyl groups or aryl groups, by reacting the compound represented by the formula (IX) with an organo-metal compound such as a compound of the formula R—MgX in the same manner as that of obtaining a compound represented by the general formula (VII), and then dehydrating this compound.

The spiropyran compounds represented by the above general formula (IV) obtained by the aforementioned process usually exist in the form of colorless or pale yellow solids or viscous liquids at normal temperature and under normal pressure, and can be confirmed by the following means (a) to (c).

(a) The kind and number of protons existing in the molecules can be learned by the nuclear magnetic resonance spectrum of protons ($H^1$-NMR). That is, a peak appears near $\delta 7$ to $8.5$ ppm due to an aromatic proton, broad peaks appear near $\delta 1.2$ to $3.5$ ppm and near $5.3$ to $3.7$ ppm due to protons of a 2-bicyclo[3,3,1]9-nonenylidene group, and a peak appears near $\delta 5.5$ to $7.0$ ppm due to protons of an alkene when $R_4$ and $R_5$ are hydrogen atoms. Further, the number of protons in the bonding group can be learned by comparing their $\delta$ peak intensities.

(b) Amounts in percent by weight of carbon, hydrogen, nitrogen, sulfur and halogen can be found by the elemental analysis. The amount in percent by weight of oxygen can be calculated by subtracting the sum of amounts in percent by weight of the above-found elements from 100. Therefore, the composition of the formed product can be determined.

(c) The kind of carbon present in the molecules can be learned by the $^{13}C$-nuclear magnetic resonance spectrum ($^{13}C$-NMR). A peak appears near $\delta 27$ to $52$ ppm due to carbon of the 2-bicyclo[3,3,1]9-nonenylidene group, a peak appears near $\delta 15$ to $35$ ppm due to carbon of the alkyl group when $R_4$ and $R_5$ are alkyl groups, and a peak appears near δ110 to 150 ppm due to carbon of an aromatic hydrocarbon group or of an unsaturated heterocyclic group.

The spiropyran compound represented by the general formula (IV) dissolves well in a general organic solvent such as a toluene, a chloroform or a tetrahydrofuran. A spiropyran compound represented by the general formula (IV) that is dissolved in such a solvent is, usually, almost colorless but develops a color or quickly turns into a densely colored compound upon irradiation with the sunlight or ultraviolet rays, and quickly returns back to the initial colorless state when the light is interrupted, thus exhibiting a good reversible photochromic action. The photochromic action of the compound of the general formula (IV) takes place even in a high molecular solid matrix, the reversing speed being in the order of seconds. Any high molecular matrix can be used provided it permits a spiropyran compound represented by the general formula (IV) to be uniformly dispersed therein. Optically preferred examples thereof include polymers such as a methyl polyacrylate, an ethyl polyacrylate, a methyl polymethacrylate, an ethyl polymethacrylate, a polystyrene, a polyacrylonitrile, a polyvinyl alcohol, a polyacrylamide, a poly(2-hydroxyethylmethacrylate), a polydimethylsiloxane, a polycarbonate, a poly(aliyldigiycol carbonate), or polymers obtained by copolymerizing monomers that form these polymers or by copolymerizing these monomers with other monomers.

As described above, the spiropyran compounds prepared from the spiropyrone compounds which are the starting materials obtained by the process of the present invention can be extensively used as a photochromic material. For example, they can be used as a variety of memory materials to substitute for silver salt photosensitive materials, and as copying materials, photosensitive materials for printing recording materials for use with a cathode-ray tube, photosensitive materials for use with a laser beam, and photosensitive materials for holography. Furthermore, the photochromic materials using the spiropyran compounds can be utilized as such materials as a photochromic lens material, an optical filter material, a display material, an actinometer and ornamental materials. When used for the photochromic lens, for instance, there is no particular limitation on the method preparation provided a uniform dimming property is obtained. Concrete examples include a method of sandwiching in the lens a polymer film in which is uniformly dispersed the photochromic material of the present invention and a method in which the compound is dissolved in, for example, a silicone oil at a temperature of 150° to 200° C. for 10 to 60 minutes so as to infiltrate into the lens surface which is then coated with a hardenable substance to obtain a photochromic lens. There can be further contrived a method in which the lens surface is coated with the polymer film which is then coated with a hardenable substance to obtain a photochromic lens.

When such a photochromic lens is to be obtained, it is desired to use a photochromic material that develops a dense color near the normal temperature upon irradiation with the sunlight. A compound suited for such a photochromic lens is the one represented by the above general formula (IV) wherein

is a divalent group derived from a naphthalene ring, a phenanthrene ring, a pyridine ring and a quinoline ring in particular a compound in which both R4 and R5 are hydrogen atoms has such a merit that the color develops densely and fades quickly.

By selecting the substituent $R_4$ or $R_5$ of the general formula (IV), furthermore, it is allowed to change the color-fading speed of the compound of the general formula (IV). For instance, when $R_4$ and $R_5$ are alkyl groups, a high color-fading speed is obtained presumably because the trans form is less established in the color-developing state. When R4 is a substituted amino group, the trans form in the color-developing state is stabilized by the resonance, and a dense color develops accompanied, however, by a slight decrease in the color-fading speed. The substituents $R_4$ and $R_5$ can be arbitrarily selected depending upon the object.

In the spiropyrone compounds obtained by the process of the present invention the group bonded to the second position of the benzopyran ring or the naphthopyran ring is a 2-bicyclo[3,3,1]9-nonelidene group as a result, the spiropyrone compounds can be obtained in very good yields.

The spiropyran compounds represented by the general formula (IV) prepared from the spiropyrone compounds which are the starting materials develop yellow or orange color from their colorless state at normal temperature or at temperatures (10° to 40° C.) slightly higher than the normal temperature upon irradiation with ultraviolet rays, return from the color-developing state back to the colorless state within short periods of time, and develop a dense color, thus exhibiting excellent photochromic properties. Therefore, the present invention is very utilizable as a process for preparing in good yields the spiropyrone compounds which are the starting materials from which the spiropyran compounds can be efficiently prepared.

EXAMPLES

The present invention will be described below in further detail by way of Examples, but it should be noted that the invention is in no way limited to these Examples only.

Example 1

A solution was prepared by dissolving 11.16 g (0.06 mol) of a 1-hydroxy-2-acetonaphthone and 8.16 g (0.06 mol) of a 2-bicyclo[3,3,1]nonene-9-one in 300 cc of toluene. The mixture was boiled for 10 hours, and water was separated by the azeotropic dehydration. After the reaction, toluene was removed under reduced pressure, and the remaining product was crystallized with acetone to obtain a spiropyrone compound of the following formula in an amount of 15.6 g (yield, 85%).

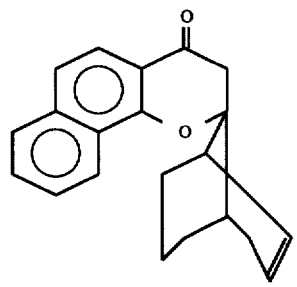

Elemental analysis of this compound indicated C 82.89%, H 6.62%, O 10.49% which were in very good agreement with the calculated values of $C_{21}H_{20}O_2$, i.e., C 82.68%, H 6.61%, O 10.51%. Furthermore the nuclear magnetic resonance spectra of protons (FIG. 1) indicated a peak of 4H near 7.2 to 8.3 ppm due to the protons of a naphthalene ring, a peak of 2H near 5.3 to 6.7 ppm due to the protons of an alkene, and broad peaks of 12H near 1.2 to 3.5 ppm due to the protons of a 2-bicyclo[3,3,1]9-nonenylidene group and protons at the third position of a spiropyrone ring. Furthermore, the $^{13}C$ nuclear magnetic resonance spectra indicated a peak near 25 to 55 ppm due to carbon of the 2-bicyclo[3,3,1]9-nonenylidene group and carbon at the third position of the spiropyrone ring, a peak near 110 to 160 ppm due to carbon of the naphthalene ring, and a peak near 80 to 140 ppm due to carbon of the alkene. It was confirmed from the above results that the isolated product was a compound represented by the above structural formula.

Example 2

A solution was prepared by dissolving 11.16 g (0.06 mol) of a 1-acetyl-2-naphthol, 8.16 g (0.06 mol) of a 2-bicyclo [3,3,1]nonene-9-one and 8.7 g (0.1 mol) of a morpholine in 300 cc of toluene. The mixture was boiled for 5 hours, and water was separated by the azeotripic dehydration. After the reaction, toluene was removed under reduced pressure, and the remaining product was crystallized with acetone to obtain a spiropyrone compound of the following formula in an amount of 14.6 g (yield, 80%).

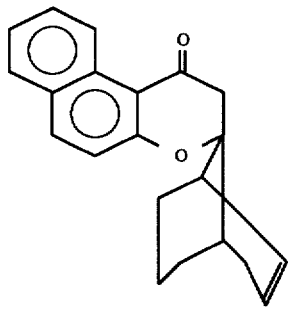

Elemental analysis of this compound indicated C 82.84%, H 6.63%, O 10.51% which were in very good agreement with the calculated values of $C_{21}H_{20}O_2$, i.e., C 89.68%, H 6.61%, O 10.51%. Furthermore, the nuclear magnetic resonance spectra of protons indicated a peak of 4H near 7.2 to 8.3 ppm due to the protons of a naphthalene ring, a peak of 2H near 5.3 to 6.7 ppm due to the protons of an alkene, and broad peaks of 12H near 1.2 to 3.5 ppm due to the protons of a 2-bicyclo[3,3,1]9-nonenylidene group and protons at the third position of a spiropyrone ring. Furthermore, the $^{13}C$ nuclear magnetic resonance spectra indicated a peak near 25 to 55 ppm due to carbon of the 2-bicyclo[3,3,1,]9-nonenylidene group and carbon at the third position of the spiropyrone ring, a peak near 110 to 160 ppm due to carbon of the naphthalene ring, and a peak near 80 to 140 ppm due to carbon of the alkene. It was confirmed from the above results that the isolated product was a compound represented by the above structural formula.

Example 3

A reaction solution obtained through the same reaction as that of Example 2 and from which water was separated, was mixed with 6.1 g of a concentrated hydrochloric acid, and was washed with water and from which the organic layer was separated. Then, toluene was removed under reduced pressure, and the remaining product was recrystallized with acetone to obtain a spiropyrone compound of the above general formula in an amount of 15.6 g (yield 85%)

Examples 4 to 26 and Comparative Examples 1 to 8

Various spiropyrone compounds were synthesized from the starting materials shown in Tables 1 and 2 in the same manner as in Example 1. The obtained spiropyrone compounds of Examples 4 to 26 were analyzed for their structures using the same means for confirming the structure as that of Example 1, and it was confirmed that the compounds were those represented by the structural formulas shown in Table I. Table 3 shows values of elemental analysis of these compounds, values calculated from the structural formulas of the compounds and characteristic absorption in the nuclear magnetic resonance spectra of protons.

TABLE 1

| Example | Starting material | Condensing Agent | Formed product | Yield (%) |
|---|---|---|---|---|
| 4 | 1-(2-hydroxy-3-cyanophenyl)ethanone | pyrrolidine | (see structure) | 77 |
| 5 | 1-(2-hydroxy-6-methoxy-4-ethylphenyl)ethanone | morpholine | (see structure) | 78 |
| 6 | 1-(2-hydroxynaphthalen-1-yl)ethanone | diethylamine | (see structure) | 80 |

TABLE 1-continued

| Example | Starting material | | Condensing Agent | Formed product | Yield (%) |
|---|---|---|---|---|---|
| 7 | (2-acetyl-1-hydroxy-8-chloronaphthalene) | (3-methoxybicycloheptenone) | thiomorpholine | chromene product with Cl and CH$_3$O | 72 |
| 8 | (acetyl hydroxyisoquinoline) | (bicycloheptenone) | N-methylpiperazine | chromene product fused to isoquinoline | 80 |
| 9 | (acetyl hydroxypyridine) | (dimethylbicycloheptenone) | pyrrolidine | chromene product with two CH$_3$ | 78 |
| 10 | (acetyl hydroxyphenylnaphthalene) | (propylbicycloheptenone) | pyrrolidine | chromene product with C$_3$H$_7$ | 80 |

TABLE 1-continued

| Example | Starting material | Condensing Agent | Formed product | Yield (%) |
|---|---|---|---|---|
| 11 | (2-hydroxy-4-phenylphenyl methyl ketone) | (3-chlorobicyclic ketone) | (ethylamine, H-N(C2H5)-H) | (chromene product with Cl) | 77 |
| 12 | (acetyl hydroxyquinoline) | (bicyclic ketone) | (pyrrolidine) | (quinoline-fused chromene product) | 80 |
| 13 | (acetyl hydroxyphenanthrene) | (dimethyl bicyclic ketone with CH3, CH3) | (pyrrolidine) | (phenanthrene-fused chromene product with CH3, CH3) | 81 |

TABLE 1-continued

| Example | Starting material | Condensing Agent | Formed product | Yield (%) |
|---|---|---|---|---|
| 14 | | | | 77 |
| 15 | | | | 75 |
| 16 | | | | 79 |

TABLE 1-continued

| Example | Starting material | Condensing Agent | Formed product | Yield (%) |
|---|---|---|---|---|
| 17 | (naphthalene with OH, C(=O)CH₃, and thiophene substituent) | bicyclic ketone | (chromene-fused product with thiophene) | 78 |
| 18 | (quinoline with OH, C(=O)CH₃, OC₃H₇) | bicyclic ketone with CF₃ | (chromene-fused product with CF₃, OC₃H₇, N) | 76 |
| 19 | (naphthalene with OH, C(=O)CH₃, and furan substituent) | bicyclic ketone with CN | (chromene-fused product with CN, furan) | 77 |

TABLE 1-continued

| Example | Starting material | | Condensing Agent | Formed product | Yield (%) |
|---|---|---|---|---|---|
| 20 | (3-bromo-5-hydroxy-1-acetylnaphthalene) | (4-butyl-2-fluorocyclohex-5-en-1-one derivative) | pyrrolidine | chromene-fused bicyclic product with Br, OH, $C_4H_9$, F substituents | 75 |
| 21 | (1-hydroxy-4-dimethylamino-2-acetylnaphthalene) | (4-benzylcyclohex-5-en-1-one derivative) | pyrrolidine | chromene-fused bicyclic product with $N(CH_3)_2$, $CH_2$-phenyl substituents | 70 |
| 22 | (2-acetyl-3-hydroxybenzothiophene) | (4-ethyl-2-ethoxycyclohex-5-en-1-one derivative) | pyrrolidine | thiochromene-fused bicyclic product with $C_2H_5$, $H_5C_2O$ substituents | 72 |

TABLE 1-continued

| Example | Starting material | Condensing Agent | Formed product | Yield (%) |
|---|---|---|---|---|
| 23 | (structure with N—CH₃, OH, C—CH₃, O) | pyrrolidine (N-H) | (product with N—CH₃, O) | 77 |
| 24 | (quinoline with OH, C—CH₃, O) | pyrrolidine (N-H) | (quinoline-fused product with Cl) | 78 |
| 25 | (furan with OH, C—CH₃, O) | pyrrolidine (N-H) | (furan-fused product with Br) | 72 |
| 26 | (thiophene with Br, OH, C—CH₃, O) | pyrrolidine (N-H) | (thiophene-fused product with Br) | 69 |

TABLE 2
| Comparative Example | Starting material | | Condensing agent | Formed product | Yield (%) |
|---|---|---|---|---|---|
| 1 | 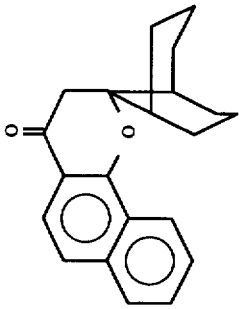 |  | 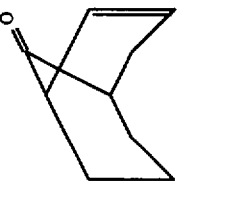 | 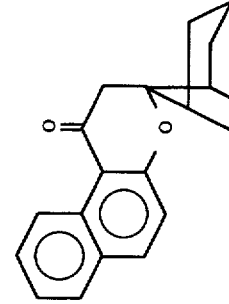 | 42 |
| 2 | 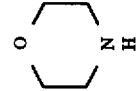 | | 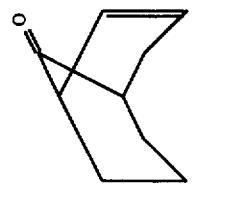 | 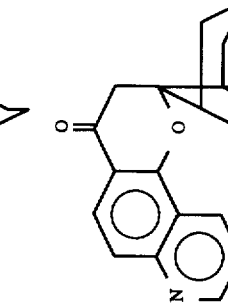 | 38 |
| 3 | 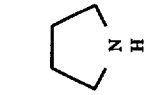 | | 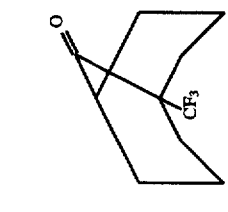 | 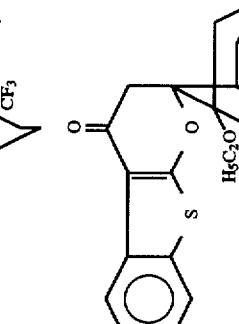 | 41 |
| 4 | 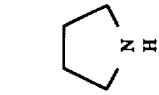 | | 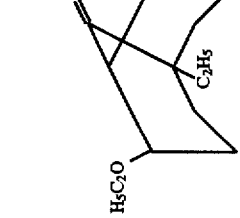 | | 40 |

TABLE 2-continued

| Comparative Example | Starting material | | Condensing agent | Formed product | Yield (%) |
|---|---|---|---|---|---|
| 5 | 1-(2-hydroxy-3-cyanophenyl)ethanone | bicyclic ketone | pyrrolidine | chromanone fused bicyclic product (CN substituent) | 42 |
| 6 | 1-(2-hydroxy-3-azapyridyl)ethanone | dimethyl-substituted bicyclic ketone | pyrrolidine | pyranopyridine fused bicyclic product (with CH₃ groups) | 47 |

TABLE 2-continued

| Comparative Example | Starting material | Condensing agent | Formed product | Yield (%) |
|---|---|---|---|---|
| 7 | (structure: furan with C(O)-CH₃ and OH) | (bromo-bicyclic ketone) | pyrrolidine | (tricyclic product with Br) | 35 |
| 8 | (1-hydroxy-2-acetyl-naphthalene with thiophene substituent) | (bicyclic ketone) | pyrrolidine | (fused product with thiophene) | 44 |

TABLE 3

| Example No. | Experimental values | | | | | | Calculated values | | | | | | 1H-NMR Spectra (ppm) |
|---|---|---|---|---|---|---|---|---|---|---|---|---|---|
| | C | H | N | O | S | others | C | H | N | O | S | others | |
| 4 | 77.08 | 6.43 | 5.03 | 11.46 | | | 77.12 | 6.47 | 5.00 | 11.41 | | | δ7.2–8.3 ppm: 3 H, δ5.5–6.7 ppm: 2 H δ1.2–3.0 ppm: 13 H |
| 5 | 76.88 | 7.72 | | 15.40 | | | 76.90 | 7.74 | | 15.36 | | | δ7.2–8.3 ppm: 2 H, δ5.5–6.7 ppm: 2 H δ1.2–3.0 ppm: 20 H |
| 6 | 79.50 | 7.23 | 4.02 | 9.22 | | | 79.51 | 7.25 | 4.03 | 9.21 | | | δ7.2–8.3 ppm: 6 H, δ5.5–6.7 ppm: 2 H δ1.2–3.5 ppm: 17 H |
| 7 | 71.66 | 5.72 | | 13.05 | | Cl 9.57 | 71.64 | 5.74 | | 13.01 | | Cl 9.61 | δ7.2–8.3 ppm: 5 H, δ5.5–6.7 ppm: 2 H δ1.2–4.0 ppm: 14 H |
| 8 | 78.70 | 6.25 | 4.61 | 10.45 | | | 78.67 | 6.27 | 4.59 | 10.48 | | | δ7.2–9.0 ppm: 5 H, δ5.5–6.7 ppm: 2 H δ1.2–3.0 ppm: 12 H |
| 9 | 76.70 | 7.81 | 4.71 | 10.78 | | | 76.74 | 7.79 | 4.71 | 10.76 | | | δ7.2–8.3 ppm: 3 H, δ5.5–6.7 ppm: 2 H δ1.2–3.5 ppm: 19 H |
| 10 | 85.24 | 7.16 | | 7.60 | | | 85.28 | 7.15 | | 7.57 | | | δ7.2–8.3 ppm: 10 H, δ5.5–6.7 ppm: 2 H δ1.2–3.0 ppm: 18 H |
| 11 | 70.68 | 5.93 | | 11.10 | | Cl 12.29 | 70.71 | 5.93 | | 11.08 | | Cl 12.28 | δ7.0–8.3 ppm: 8 H, δ5.5–6.7 ppm: 2 H δ1.2–3.0 ppm: 13 H |
| 12 | 78.71 | 6.24 | 4.62 | 10.44 | | | 78.67 | 6.27 | 4.59 | 10.48 | | | δ7.2–9.0 ppm: 5 H, δ5.5–6.7 ppm: 2 H δ6.2–3.0 ppm: 12 H |
| 13 | 84.41 | 7.60 | | 8.07 | | | 84.39 | 7.58 | | 8.03 | | | δ7.2–8.3 ppm: 8 H, δ5.5–6.7 ppm: 2 H δ1.2–3.0 ppm: 20 H |
| 14 | 71.74 | 6.68 | 3.22 | 18.37 | | | 71.71 | 6.71 | 3.22 | 18.37 | | | δ7.2–8.3 ppm: 4 H, δ5.5–6.7 ppm: 2 H δ1.2–2.5 ppm: 23 H |
| 15 | 74.65 | 6.91 | | 6.60 | F | 11.84 | 74.67 | 6.89 | | 6.63 | F | 11.81 | δ7.2–8.5 ppm: 4 H, δ5.5–6.7 ppm: 2 H δ1.2–4.5 ppm: 27 H |
| 16 | 86.83 | 6.21 | | 6.96 | | | 86.81 | 6.18 | | 7.01 | | | δ7.2–8.3 ppm: 15H, δ5.5–6.7 ppm: 2 H δ1.2–3.5 ppm: 11 H |
| 17 | 77.64 | 5.74 | | 8.32 | 8.30 | | 77.69 | 5.73 | | 8.28 | 8.30 | | δ7.2–9.0 ppm: 8 H, δ5.5–7.0 ppm: 2 H δ1.2–3.0 ppm: 12 H |
| 18 | 66.82 | 5.55 | 3.22 | 11.16 | | F 12.25 | 66.81 | 5.60 | 3.25 | 11.13 | | F 13.21 | δ7.0–9.0 ppm: 4 H, δ5.5–6.7 ppm: 2 H δ1.2–4.5 ppm: 18 H |
| 19 | 79.00 | 5.35 | 3.49 | 12.14 | | | 78.97 | 5.35 | 3.54 | 12.14 | | | δ7.2–9.0 ppm: 8 H, δ5.5–6.7 ppm: 2 H δ1.2–3.0 ppm: 11 H |
| 20 | 63.39 | 5.54 | | 10.14 | F Br | 4.02 16.90 | 63.43 | 5.53 | | 10.14 | F Br | 4.01 16.88 | δ7.2–8.3 ppm: 5 H, δ5.5–6.7: 2 H δ1.2–3.0 ppm: 19 H |
| 21 | 82.36 | 7.16 | 3.23 | 7.31 | | | 82.35 | 7.14 | 3.20 | 7.31 | | | δ7.2–8.3 ppm: 10 H, δ5.5–6.7 ppm: 2 H δ1.2–3.5 ppm: 19 H |
| 22 | 72.75 | 6.82 | | 12.54 | 8.39 | | 72.72 | 6.85 | | 12.55 | 8.38 | | δ7.2–9.0 ppm: 4 H, δ5.5–6.7 ppm: 2 H δ1.2–4.5 ppm: 20 H |
| 23 | 74.65 | 7.47 | 5.41 | 12.47 | | | 74.68 | 7.44 | 5.44 | 12.44 | | | δ7.2–8.3 ppm: 2 H, δ5.5–6.7 ppm: 2 H δ1.2–3.5 ppm: 15 H |
| 24 | 70.66 | 5.36 | 4.15 | 9.44 | | Cl 10.39 | 70.69 | 5.34 | 4.12 | 9.42 | | Cl 10.43 | δ6.9–9.0 ppm: 5 H, δ5.5–6.7 ppm: 2 H δ1.2–3.0 ppm: 11 H |
| 25 | 55.77 | 4.70 | | 14.88 | | Br 24.73 | 55.75 | 4.68 | | 14.85 | | Br 24.72 | δ7.2–9.0 ppm: 2 H, δ5.5–6.7 ppm: 2 H δ1.2–2.5 ppm: 11 H |
| 26 | 53.15 | 4.42 | | 9.41 | 9.45 | Br 23.57 | 53.11 | 4.45 | | 9.44 | 9.45 | Br 23.55 | δ7.0–9.0 ppm: 1 H, δ5.5–6.7 ppm: 2 H δ1.2–3.0 ppm: 12 H |

Application Example 1

15.6 Grams (0.051 mol) of the spiropyrone compound of the following formula obtained in Example 1

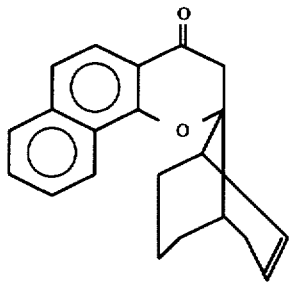

was dissolved in 200 cc of methanol, followed by the gradual addition of 3.42 g (0.09 mol) of a sodium boron hydride at a temperature of 65° C. to carry out the reaction for 4 hours to obtain a 4-hydroxypiran compound. 17.4 Grams of the 4-hydroxypiran compound was heated together with 15 g of anhydrous copper sulfate in a stream of carbon dioxide at a temperature of 150° to 160° C. for 10 minutes, and a brown viscous liquid was refined by chromatography on the silica gel to obtain a spiropyran compound of the following formula in an amount of 13.3 g. The yield of the spiropyran compound was 77% with respect to the amount of the 1-hydroxy-2-acetonaphtone that was used.

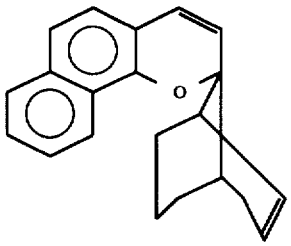

Figure 2:
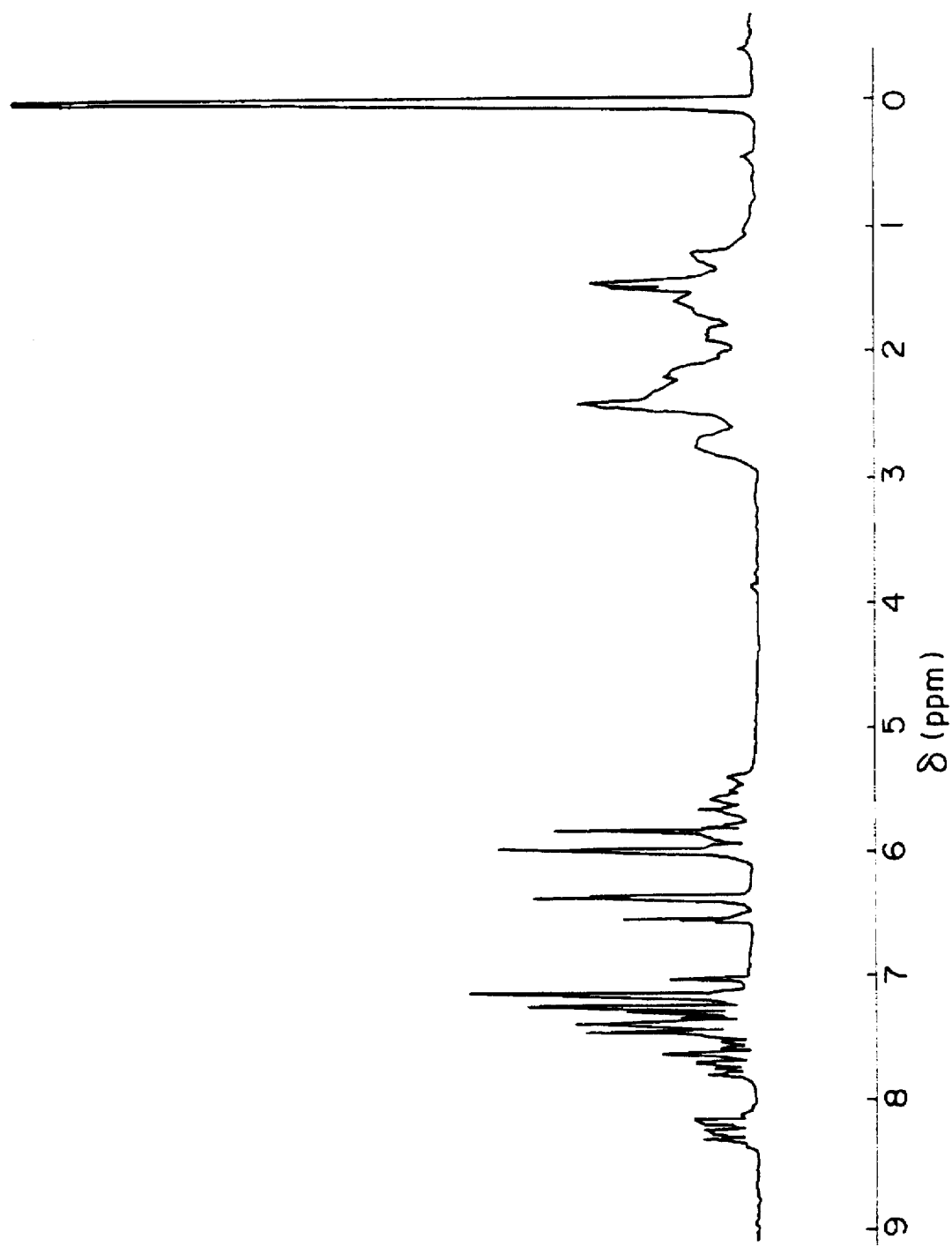
FIG. 2 is a chart of nuclear magnetic resonance spectra of protons of a spiropyran compound obtained in Application Example 1.

Elemental analysis of this compound indicated C 87.84%, H 7.04%, O 5.62% which were in very good agreement with the calculated values of $C_{21}H_{20}O$, i.e., C 87.46%, H 6.99%, O 5.55%. Furthermore the nuclear magnetic resonance spectra of protons (FIG. 2) indicated a peak of 6H near 7.2 to 8.3 ppm due to the protons of a naphthalene ring, a peak of 4H near 5.3 to 6.7 ppm due to the protons of an alkene, and a broad peak of 10H near 1.2 to 3.0 ppm due to the protons of a 2-bicyclo[3,3,1]9-noneylidene group and protons at the third position of a spiropyrone ring. Furthermore, the $^{13}C$ nuclear magnetic resonance spectra indicated a peak near 25 to 55 ppm due to carbon of the 2-bicyclo[3,3,1]9-nonenylidene group, a peak near 110 to 160 ppm due to carbon of the naphthalene ring, and a peak near 80 to 140 ppm due to carbon of the alkene. It was confirmed from the above results that the isolated product was a compound represented by the above structural formula.

Application Example 2

14.6 Grams (0.048 mol) of the spiropyrone compound of the following formula obtained in Example 2

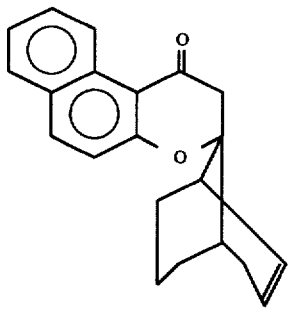

was dissolved in 200 cc of methanol, followed by the gradual addition of 2.74 g (0.072 mol) of an aluminum lithium hydride at a temperature of 65° C. to carry out the reaction for 4 hours to obtain a 4-hydroxypiran compound of the following formula.

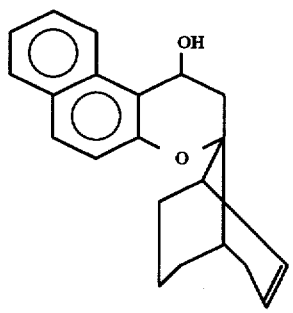

14.0 Grams of the 4-hydroxypiran compound was heated together with 15 g of anhydrous copper sulfate in a stream of carbon dioxide at a temperature of 170° to 180° C. for 10 minutes, and a brown viscous liquid was refined by chromatography on the silica gel to obtain a spiropyran compound of the following formula in an amount of 12.6 g. The yield of the spiropyran compound was 72% with respect to the amount of the 1-acetyl-2-naphthol that was used.

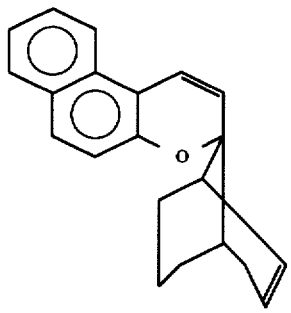

Elemental analysis of this compound indicated C 87.36%, H 7.02%, O 5.62% which were in very good agreement with the calculated values of $C_{21}H_{20}O$, i.e., C 87.46%, H 6.99%, O 5.55%. Furthermore, the nuclear magnetic resonance spectra of protons indicated a peak of 6H near 7.2 to 8.3 ppm due to the protons of a naphthalene ring, a peak of 4H near 5.5 to 7.0 ppm due to the protons of an alkene, and a broad peak of 10H near 1.2 to 3.0 ppm due to the protons of a 2-bicyclo[3,3,1]9-nonenylidene group. Furthermore, the 13C nuclear magnetic resonance spectra indicated a peak near 27 to 55 ppm due to carbon of the 2-bicyclo[3,3,1]9-nonenylidene group, a peak near 110 to 160 ppm due to carbon of the naphthalene ring, and a peak near 80 to 140 ppm due to carbon of the alkene. It was confirmed from the above results that the isolated product was a compound represented by the above structural formula.

Application Example 3

3.04 Grams (0.01 mol) of a spiropyrone compound of the following formula obtained in the same manner as in Example 2

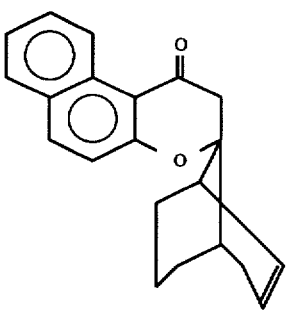

was dissolved in 50 cc of anhydrous ether. The solution was then cooled to 0° C., and a Grignard reagent $CH_3MgI$ (0.012 mol) newly prepared in 50 cc of anhydrous ether was dropewisely added to the solution over a time of about one hour. After the dropwise addition has been finished, the solution was stirred at room temperature for another two hours. The ether solution was then calmly poured into cold water, the product was extracted with ether, the solution was dried with magnesium sulfate, the ether was removed under reduced pressure, and the spiropyrone compound was transformed into a 4-hydroxypyran compound of the following formula.

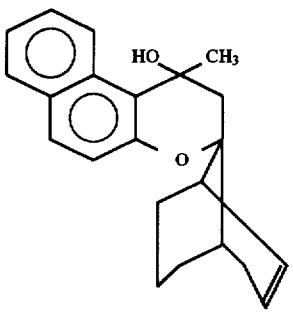

2.9 Grams of the 4-hydroxypyran compound was heated together with 3 g of anhydrous copper sulfate at 200° C. for about 10 minutes in a stream of carbon dioxide, and a brown viscous solution was refined by chromatography on silica gel to obtain 2.57 g of a spiropyran compound on the following formula. The yield of the spiropyran compound was 68% with respect to the amount of the 1-acetyl-2-naphthol that was used.

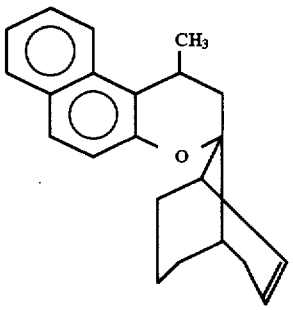

Through the elemental analysis, magnetic resonance spectra of protons and $^{13}$C-nuclear magnetic resonance spectra carried out in the same manner as in Example 1, it was confirmed that the compound was the one represented by the above structural formula. Table 5 shows values of elemental analysis of this compound and values calculated from the composition formula of this compound.

Application Example 4

30.4 Grams (0.1 mol) of a spiropyrone compound of the following formula

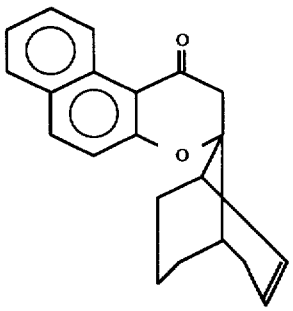

was prepared in the same manner as in Example 2, and to the reaction solution was further added 8.7 g (0.1 mol) of morpholine to continue the reaction for 10 hours. After the reaction, the toluene was removed under reduced pressure, and the remaining product was recrystallized with acetone to obtain 35.3 g of a compound represented by the following formula. The yield of the spiropyran compound was 82% with respect to the amount of the 1-acetyl-2-naphthol that was used.

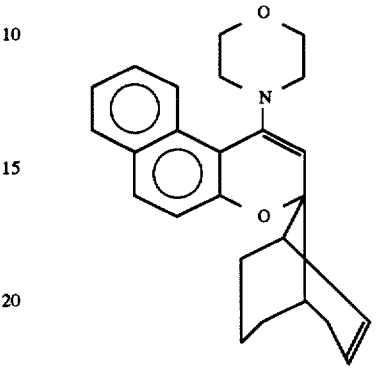

Through the elemental analysis, magnetic resonance spectra of protons and $^{13}$C-nuclear magnetic resonance spectra carried out in the same manner as in Example 1, it was confirmed that the compound was the one represented by the above structural formula. Table 5 shows values of elemental analysis of this compound and values calculated from the composition formula of this compound.

Application Example 5

17.9 Grams (0.052 mol) of the spiropyran compound obtained in Application Example 4 was dissolved in 100 cc of methanol and was reacted with 8.12 g of a methyl iodide (0.057 mol) at a temperature of 10° C. for 5 hours to obtain 15.6 g of a spiropyrone compound represented by the following formula.

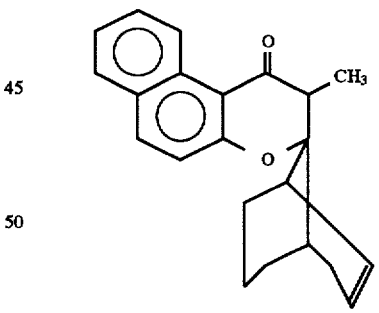

The thus formed spiropyrone compound was transformed into a 4-hydroxypyran compound in the same manner as in Application Example 1, subjected to the dehydration reaction, separated and was refined to obtain 13.3 g of a spiropyran compound of the following formula. The yield of the spiropyran compound was 68% with respect to the amount of the 1-acetyl-2-naphthol that was used.

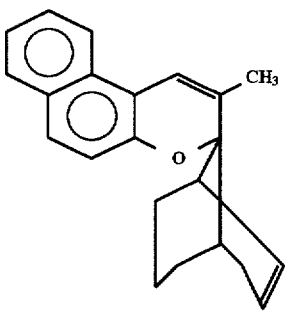

Through the elemental analysis, magnetic resonance spectra of protons and $^{13}$C-nuclear magnetic resonance spectra carried out in the same manner as in Example 1, it was confirmed that the compound was the one represented by the above structural formula. Table 5 shows values of elemental analysis of this compound and values calculated from the composition formula of this compound.

Application Example 6

15.6 Grams (0.049 mol) of a spiropyrone compound of the following formula obtained in the same manner as in Application Example 5 was reacted with CH$_3$MgI in the same manner as in Application Example 3 to obtain 4-hydroxypiran compound

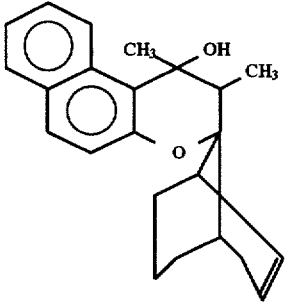

and was then subjected to the dehydration reaction to obtain 13.2 g of a spiropyran compound of the following formula.

The yield of the spiropyran compound was 68% with respect to the amount of the 1-acetyl-2-naphthol that was used.

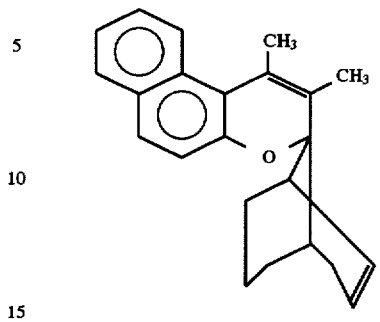

Through the elemental analysis, magnetic resonance spectra of protons and $^{13}$C-nuclear magnetic resonance spectra carried out in the same manner as in Example 1, it was confirmed that the compound was the one represented by the above structural formula. Table 5 shows values of elemental analysis of this compound and values calculated from the composition formula of this compound.

Application Examples 7 to 42

Various spiropyran compounds were synthesized in the same manner as in Application Examples 1 to 6 from the spiropyrone compounds shown in Table 4 obtained in Examples 4 to 26. In Table 4, however, Application Examples 7 to 11 were carried out in the same manner as in Application Example 4, Application Examples 12 to 27 were carried out in the same manner as in Application Example 1 or 2, Application Examples 28 to 32 were carried out in the same manner as in Application Example 3, Application Examples 33 to 37 were carried out in the same manner as in Application Example 5, and Application Examples 38 to 42 were carried out in the same manner as in Application Example 6.

Analysis of the structures using the same means for confirming the structures as that of Example 1 indicated that the formed products were the compounds represented by the structural formulas shown in Table 4. Table 5 shows values of elemental analysis of the compounds, values calculated from the structural formulas of the compounds and characteristic absorption in the infrared-ray absorption spectrum.

TABLE 4

| Application Example | Starting material | | Formed product | Yield (%) |
|---|---|---|---|---|
| 7 | Example 4 | pyrrolidine (NH) | | 70 |
| 8 | Example 5 | morpholine (NH) | | 70 |
| 9 | Example 6 | HN(C$_2$H$_5$)$_2$ | | 76 |

TABLE 4-continued

| Application Example | Starting material | | Formed product | Yield (%) |
|---|---|---|---|---|
| 10 | Example 7 | | | 74 |
| 11 | Example 8 | | | 71 |
| 12 | Example 9 | — | | 73 |

TABLE 4-continued

| Application Example | Starting material | Formed product | Yield (%) |
|---|---|---|---|
| 13 | Example 4 | | 71 |
| 14 | Example 10 | | 74 |
| 15 | Example 11 | | 70 |
| 16 | Example 12 | | 72 |

TABLE 4-continued

| Application Example | Starting material | | Formed product | Yield (%) |
|---|---|---|---|---|
| 17 | Example 13 | — | | 74 |
| 18 | Example 14 | — | | 69 |
| 19 | Example 15 | — | | 68 |

TABLE 4-continued
| Application Example | Starting material | Formed product | Yield (%) |
|---|---|---|---|
| 20 | Example 16 | — | 70 |
| 21 | Example 17 | — | 67 |
| 22 | Example 18 | — | 66 |
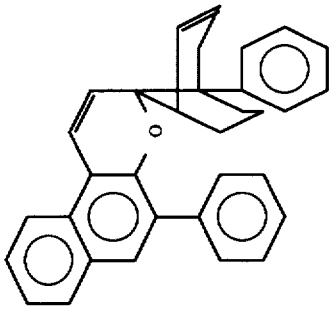

TABLE 4-continued

| Application Example | Starting material | | Formed product | Yield (%) |
|---|---|---|---|---|
| 23 | Example 19 | — | | 67 |
| 24 | Example 20 | — | | 65 |
| 25 | Example 21 | — | | 64 |

TABLE 4-continued

| Application Example | Starting material | | Formed product | Yield (%) |
|---|---|---|---|---|
| 26 | Example 22 | — | (structure with thiophene, benzene fused ring, bridged bicyclic with C₂H₅ and H₅C₂O substituents, alkene) | 66 |
| 27 | Example 23 | — | (N-CH₃ pyridine fused bridged bicyclic structure with alkene) | 67 |
| 28 | Example 24 | PhCH₂MgBr | (quinoline with CH₂-phenyl substituent attached to bridged bicyclic with Cl, alkene) | 66 |

Starting material structures:
- Example 22: thiophene-benzofused ketone with bridged bicyclic bearing C₂H₅ and H₅C₂O
- Example 23: N-CH₃ pyridine-fused ketone with bridged bicyclic
- Example 24: quinoline-fused ketone with bridged bicyclic bearing Cl TABLE 4-continued

| Application Example | Starting material | | Formed product | Yield (%) |
|---|---|---|---|---|
| 29 | Example 4 | CH₃CH₂CH₂CH₂MgBr | | 68 |
| 30 | Example 9 | [phenyl]MgBr | | 70 |
| 31 | Example 10 | C₂H₅MgBr | | 71 |

TABLE 4-continued
| Application Example | Starting material | | Formed product | Yield (%) |
|---|---|---|---|---|
| 32 | Example 1 | C$_4$H$_7$MgBr | | 74 |
| 33 | Example 2 | CH$_3$CH$_2$CH$_2$Br | | 69 |
| 34 | Example 2 | PhCH$_2$CH$_2$Br | | 67 |
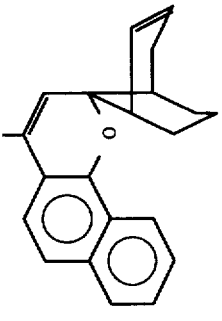

TABLE 4-continued

| Application Example | Starting material | | Formed product | Yield (%) |
|---|---|---|---|---|
| 35 | Example 2 | CH₃\CHBr / CH₃ | | 70 |
| 36 | Example 2 | 4-I-C₆H₄-OCH₃ | | 69 |
| 37 | Example 24 | C₂H₅I | | 70 |

TABLE 4-continued

| Application Example | Starting material | | | Formed product | Yield (%) |
|---|---|---|---|---|---|
| 38 | Example 25 | CH$_3$I | CH$_3$MgBr | | 62 |
| 39 | Example 26 | (phenyl)-CH$_2$I | C$_2$H$_5$MgBr | | 60 |
| 40 | Example 2 | CH$_3$CH$_2$CH$_2$I | (phenyl)-CH$_2$MgBr | | 61 |

TABLE 4-continued

| Application Example | Starting material | | Formed product | Yield (%) |
|---|---|---|---|---|
| 41 | Example 2 | CH₂CH₂I–C₆H₅ / C₆H₅–MgBr | | 60 |
| 42 | Example 1 | C₂H₅I / C₂H₅MgBr | | 63 |

TABLE 5

| Application Example No. | \multicolumn{6}{c}{Experimental values} | \multicolumn{6}{c}{Calculated values} | $^1$H-NMR Spectra (ppm) |
|---|---|---|---|---|---|---|---|---|---|---|---|---|---|

| Application Example No. | C | H | N | O | S | others | C | H | N | O | S | others | $^1$H-NMR Spectra (ppm) |
|---|---|---|---|---|---|---|---|---|---|---|---|---|---|
| 1 | 87.34 | 7.04 | | 5.62 | | | 87.46 | 6.99 | | 5.55 | | | δ7.0–8.3 ppm: 6 H, δ5.5–6.7 ppm: 4 H δ1.2–3.0 ppm: 10 H |
| 2 | 87.36 | 7.02 | | 5.62 | | | 87.46 | 6.99 | | 5.55 | | | δ7.2–8.3 ppm: 6 H, δ5.5–6.7 ppm: 4 H δ1.2–3.0 ppm: 10 H |
| 3 | 87.28 | 7.38 | | 5.34 | | | 87.38 | 7.33 | | 5.29 | | | δ7.2–8.3 ppm: 6 H, δ5.5–7.0 ppm: 3 H δ1.2–3.0 ppm: 13 H |
| 4 | 80.35 | 7.29 | 3.77 | 8.59 | | | 80.40 | 7.28 | 3.75 | 8.57 | | | δ7.2–8.3 ppm: 6 H, δ5.5–7.2 ppm: 3 H δ1.2–3.0 ppm: 18 H |
| 5 | 87.40 | 7.31 | | 5.33 | | | 87.38 | 7.33 | | 5.29 | | | δ7.2–8.3 ppm: 6 H, δ5.5–6.7 ppm: 3 H δ1.2–3.0 ppm: 13 H |
| 6 | 87.32 | 7.63 | | 5.05 | | | 87.30 | 7.64 | | 5.06 | | | δ7.2–8.3 ppm: 6 H, δ5.5–6.7 ppm: 2 H δ1.2–3.5 ppm: 16 H |
| 7 | 79.50 | 7.30 | 8.40 | 4.80 | | | 79.49 | 7.27 | 8.43 | 4.81 | | | δ7.2–8.0 ppm: 3 H, δ5.5–6.7 ppm: 3 H δ1.2–4.0 ppm: 18 H |
| 8 | 75.44 | 8.21 | 3.72 | 12.63 | | | 75.44 | 8.21 | 3.72 | 12.63 | | | δ7.0–7.8 ppm: 2 H, δ5.5–6.7 ppm: 3 H δ1.2–4.5 ppm: 26 H |
| 9 | 80.65 | 8.29 | 7.00 | 4.06 | | | 80.76 | 8.28 | 6.98 | 3.98 | | | δ7.2–8.3 ppm: 6 H, δ5.5–6.7 ppm: 3 H δ1.2–4.5 ppm: 25 H |
| 10 | 68.30 | 5.90 | 3.25 | 7.28 | 7.28 | Cl 8.06 | 68.23 | 5.95 | 3.18 | 7.27 | 7.28 | Cl 8.06 | δ7.2–8.3 ppm: 5 H, δ5.5–6.7 ppm: 3 H δ1.2–4.5 ppm: 18 H |
| 11 | 77.49 | 7.52 | 10.86 | 4.13 | | | 77.49 | 7.54 | 10.84 | 4.13 | | | δ7.2–8.3 ppm: 5 H, δ5:5–6.7 ppm: 3 H δ1.2–4.5 ppm: 21 H |
| 12 | 81.09 | 8.24 | 4.98 | 5.69 | | | 81.10 | 8.24 | 5.00 | 5.69 | | | δ7.2–9.0 ppm: 3 H, δ5.5–6.7 ppm: 4 H δ1.2–3.0 ppm: 17 H |
| 13 | 82.06 | 6.56 | 5.30 | 6.10 | | | 82.10 | 6.51 | 5.32 | 6.08 | | | δ7.0–7.8 ppm: 3 H, δ5.5–6.7 ppm: 4 H δ1.2–3.0 ppm: 10 H |
| 14 | 88.63 | 7.44 | | 3.94 | | | 88.63 | 7.44 | | 3.94 | | | δ7.2–8.3 ppm: 10 H, δ5.5–7.0 ppm: 4 H δ1.2–3.0 ppm: 16 H |
| 15 | 79.15 | 6.05 | | 4.60 | | Cl 10.18 | 79.18 | 6.07 | | 4.59 | | Cl 10.16 | δ7.0–7.8 ppm: 8 H, δ5.5–6.7 ppm: 4 H δ1.2–3.0 ppm: 9 H |
| 16 | 83.00 | 6.63 | 4.81 | 5.56 | | | 83.01 | 6.62 | 4.84 | 5.53 | | | δ6.9–9.0 ppm: 5 H, δ5.5–6.7 ppm: 4 H δ1.2–3.0 ppm: 10 H |
| 17 | 88.38 | 7.42 | | 4.20 | | | 88.38 | 7.42 | | 4.20 | | | δ7.2–8.3 ppm: 8 H, δ5.5–6.7 ppm: 4 H δ1.2–3.0 ppm: 16 H |
| 18 | 74.56 | 6.95 | 3.36 | 15.13 | | | 74.44 | 6.97 | 3.34 | 15.26 | | | δ7.2–8.3 ppm: 4 H, δ5.5–6.7 ppm: 4 H δ1.2–4.5 ppm: 21 H |
| 19 | 77.20 | 7.15 | | 3.35 | | F 12.20 | 77.23 | 7.13 | | 3.43 | | F 12.22 | δ7.2–8.3 ppm: 4 H, δ5.5–6.7 ppm: 4 H δ1.2–3.5 ppm: 25 H |
| 20 | 89.85 | 6.38 | | 3.77 | | | 89.96 | 6.41 | | 3.63 | | | δ7.2–8.3 ppm: 15 H, δ5.5–6.7 ppm: 4 H δ1.2–3.0 ppm: 9 H |
| 21 | 81.00 | 6.00 | | 4.38 | 8.62 | | 81.04 | 5.98 | | 4.32 | 8.65 | | δ7.1–9.0 ppm: 8 H, δ5.5–6.7 ppm: 4 H δ1.2–3.0 ppm: 10 H |
| 22 | 69.50 | 5.76 | 3.46 | 7.90 | | F 13.38 | 69.39 | 5.82 | 3.37 | 7.70 | | F 13.72 | δ6.9–9.0 ppm: 4 H, δ5.5–6.7 ppm: 4 H δ1.2–4.5 ppm: 16 H |
| 23 | 82.25 | 5.55 | 3.71 | 8.45 | | Cl 10.39 | 70.69 | 5.34 | 4.12 | 9.42 | | Cl 10.43 | δ7.2–8.7 ppm: 5 H, δ5.5–6.7 ppm: 7 H δ1.2–3.5 ppm: 9 H |
| 24 | 65.65 | 5.73 | | 7.0 | | F 4.15 Br 17.47 | 65.65 | 5.73 | | 7.00 | | F 4.15 Br 17.47 | δ7.2–8.3 ppm: 5 H, δ5.5–6.7 ppm: 4 H δ1.2–3.0 ppm: 17 H |
| 25 | 85.40 | 7.36 | 3.40 | 3.84 | | | 85.47 | 7.41 | 3.32 | 3.80 | | | δ7.2–8.3 ppm: 10 H, δ5.5–6.7 ppm: 4 H δ1.2–4.5 ppm: 17 H |
| 26 | 75.40 | 7.21 | | 8.70 | 8.69 | | 75.37 | 7.15 | | 8.73 | 8.75 | | δ7.2–9.0 ppm: 4 H, δ5.5–6.7 ppm: 4 H δ1.2–4.5 ppm: 18 H |
| 27 | 80.01 | 7.51 | 5.83 | 6.65 | | | 79.97 | 7.55 | 5.83 | 6.66 | | | δ7.2–9.0 ppm: 2 H, δ5.5–6.7 ppm: 4 H δ1.2–3.5 ppm: 13 H |
| 28 | 78.35 | 5.82 | 3.35 | 3.89 | | Cl 8.59 | 78.34 | 5.84 | 3.38 | 3.87 | | Cl 8.57 | δ6.9–9.0 ppm: 10 H, δ5.5–7.0 ppm: 3 H δ1.2–4.8 ppm: 11 H |
| 29 | 82.70 | 7.80 | 4.46 | 5.04 | | | 82.72 | 7.89 | 4.38 | 5.01 | | | δ7.0–7.8 ppm: 3 H, δ5.5–6.7 ppm: 3 H δ1.2–3.5 ppm: 19 H |
| 30 | 84.03 | 7.63 | 3.90 | 4.44 | | | 84.00 | 7.61 | 3.92 | 4.47 | | | δ7.0–8.9 ppm: 8 H, δ5.5–7.0 ppm: 3 H δ1.2–3.0 ppm: 10 H |
| 31 | 88.42 | 7.88 | | 3.66 | | | 88.44 | 7.88 | | 3.68 | | | δ7.2–8.3 ppm: 9 H, δ5.5–6.7 ppm: 3 H δ1.2–3.5 ppm: 22 H |
| 32 | 87.64 | 7.66 | | 4.70 | | | 87.68 | 7.65 | | 4.67 | | | δ7.2–8.3 ppm: 6 H, δ5.5–6.7 ppm: 3 H δ1.2–3.5 ppm: 17 H |
| 33 | 87.22 | 7.96 | | 4.81 | | | 87.22 | 7.93 | | 4.84 | | | δ7.2–8.3 ppm: 6 H, δ5.5–6.7 ppm: 3 H δ1.2–3.5 ppm: 17 H |
| 34 | 88.60 | 7.26 | | 4.14 | | | 88.73 | 7.19 | | 4.07 | | | δ7.2–8.3 ppm: 11 H, δ5.5–6.7 ppm: 3 H δ1.2–3.5 ppm: 14 H |
| 35 | 87.21 | 7.95 | | 4.84 | | | 87.23 | 7.93 | | 4.84 | | | δ7.2–8.3 ppm: 6 H, δ5.5–6.7 ppm: 3 H δ1.2–3.5 ppm: 17 H |
| 36 | 85.20 | 6.66 | | 8.14 | | | 85.25 | 6.64 | | 8.11 | | | δ7.2–8.3 ppm: 10 H, δ5.5–7.0 ppm: 3 H δ1.2–4.5 ppm: 13 H |

TABLE 5-continued

| Application Example No. | Values (%) of elemental analysis | | | | | | | | | | | | ¹H-NMR Spectra (ppm) |
|---|---|---|---|---|---|---|---|---|---|---|---|---|---|
| | Experimental values | | | | | | Calculated values | | | | | | |
| | C | H | N | O | S | others | C | H | N | O | S | others | |
| 37 | 83.22 | 7.31 | 4.45 | 5.03 | | | 83.25 | 7.30 | 4.41 | 5.04 | | | δ7.2–9.0 ppm: 5 H, δ3.5–7.0 ppm: 5 H δ1.2–3.5 ppm: 13 H |
| 38 | 60.90 | 5.72 | | 9.56 | | Br 23.86 | 60.91 | 5.71 | | 9.54 | | Br 23.84 | δ7.2–9.0 ppm: 2 H, δ5.5–7.0 ppm: 2 H δ1.2–3.0 ppm: 15 H |
| 39 | 65.25 | 5.72 | | 3.63 | 7.28 | Br 18.11 | 65.30 | 5.71 | | 3.62 | 7.26 | Br 18.10 | δ7.2–9.0 ppm: 6 H, δ5.5–7.0 ppm: 2 H δ1.2–4.0 ppm: 17 H |
| 40 | 88.55 | 7.68 | | 3.85 | | | 88.53 | 7.66 | | 3.81 | | | δ7.0–8.3 ppm: 11 H, δ5.5–7.0 ppm: 2 H δ1.2–3.5 ppm: 19 H |
| 41 | 89.68 | 6.89 | | 3.43 | | | 89.71 | 6.88 | | 3.41 | | | δ7.0–8.9 ppm: 16 H, δ5.5–7.0 ppm: 2 H δ1.2–3.5 ppm: 14 H |
| 42 | 87.22 | 8.16 | | 4.62 | | | 87.17 | 8.19 | | 4.64 | | | δ7.2–8.3 ppm: 6 H, δ5.5–7.0 ppm: 2 H δ1.2–3.0 ppm: 20 H |

Application Example 43

The spiropyran compound of the following formula synthesized in Application Example 1

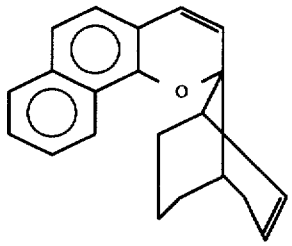

was dissolved and decomposed in a methyl polymethacrylate using benzene, and was casted onto a slide glass (11.2×3.7 cm) to form a film thereon. The concentration of the above compound contained in the film was adjusted to be $1.0\times10^{-4}$ mol/g and the thickness was adjusted to be 0.1 mm. The photochromic film was exposed to the light of a mercury lamp SHL-100 produced by Toshiba Co. at a temperature of 25° C.+1° C. from a distance of 10 cm for 60 seconds so as to develop a color, in order to measure its photochromic properties. The photochromic properties were expressed as described below. The results were as shown in Table 6.

Max. absorption wavelength (λmax)

λmax of the color-developing film was found by using a spectrophotometer 220A manufactured by Hitachi, Ltd.

ε(60 seconds)

Absorbancy of the film at a maximum absorption wavelength after irradiated with light for 60 seconds under the above-mentioned conditions.

ε(0 second)

Absorbancy of the film that is not irradiated with light at a maximum absorption wave of when it is irradiated with light.

Half-value period $t^{1/2}$

Time needed until the absorbancy of the film decreases to one-half {ε(60 sec)-ε(0 sec)} after irradiated with light for 60 seconds.

Application Examples 43 to 84

Compounds prepared in Application Examples 2 to 42 were measured for their photochromic properties in the same manner as in Application Example 1. The results were as shown in Table 6.

TABLE 6

| Application Example | Spiropyran compound | Developed color tone | ε (60 sec.) −ε (0 sec.) | λ MAX (nm) | t½ (sec.) |
|---|---|---|---|---|---|
| 43 | 1 | yellow | 1.0 | 450 | 115 |
| 44 | 2 | yellow | 0.9 | 403 | 58 |
| 45 | 3 | yellow | 0.7 | 454 | 36 |
| 46 | 4 | yellow | 1.0 | 408 | 185 |
| 47 | 5 | yellow | 0.9 | 454 | 36 |
| 48 | 6 | yellow | 0.8 | 450 | 30 |
| 49 | 7 | orange | 0.7 | 476 | 125 |
| 50 | 8 | orange | 0.8 | 483 | 127 |
| 51 | 9 | yellow | 1.0 | 408 | 180 |
| 52 | 10 | yellow | 1.0 | 410 | 140 |
| 53 | 11 | yellow | 1.2 | 442 | 175 |
| 54 | 12 | yellow | 0.8 | 450 | 50 |
| 55 | 13 | orange | 1.2 | 478 | 110 |
| 56 | 14 | yellow | 1.0 | 440 | 118 |
| 57 | 15 | orange | 0.6 | 470 | 113 |
| 58 | 16 | yellow | 1.0 | 436 | 142 |
| 59 | 17 | yellow | 1.0 | 456 | 138 |
| 60 | 18 | red | 1.1 | 498 | 110 |
| 61 | 19 | yellow | 1.1 | 450 | 125 |
| 62 | 20 | orange | 1.0 | 460 | 70 |
| 63 | 21 | red | 1.1 | 490 | 107 |
| 64 | 22 | orange | 0.9 | 472 | 55 |
| 65 | 23 | red | 1.0 | 505 | 103 |
| 66 | 24 | yellow | 1.0 | 430 | 62 |
| 67 | 25 | red | 1.0 | 486 | 106 |
| 68 | 26 | yellow | 0.9 | 448 | 98 |
| 69 | 27 | orange | 1.0 | 470 | 48 |
| 70 | 28 | yellow | 0.9 | 402 | 16 |
| 71 | 29 | orange | 0.5 | 494 | 11 |
| 72 | 30 | orange | 0.6 | 480 | 26 |
| 73 | 31 | yellow | 0.7 | 460 | 90 |
| 74 | 32 | yellow | 0.8 | 445 | 110 |
| 75 | 33 | yellow | 0.6 | 410 | 18 |
| 76 | 34 | yellow | 0.7 | 406 | 26 |
| 77 | 35 | yellow | 0.6 | 410 | 18 |
| 78 | 36 | yellow | 0.9 | 420 | 25 |
| 79 | 37 | yellow | 0.5 | 415 | 22 |
| 80 | 38 | yellow | 0.6 | 430 | 10 |
| 81 | 39 | orange | 0.6 | 465 | 12 |
| 82 | 40 | yellow | 0.8 | 420 | 14 |
| 83 | 41 | yellow | 0.7 | 440 | 17 |
| 84 | 42 | yellow | 1.0 | 450 | 28 |

We claim:

1. A process for preparing a spiropyrone compound represented by the following general formula (III)

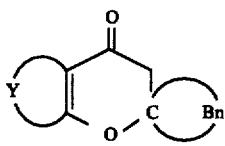
(III)

wherein

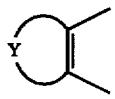

is a substituted or an unsubstituted aromatic hydrocarbon group or a substituted or an unsubstituted unsaturated heterocyclic group, and

is a substituted or an unsubstituted 2-bicyclo[3,3,1]9-nonenylidene group, comprising reacting in the presence of a primary or secondary amine condensing agent a compound represented by the following general formula (I)

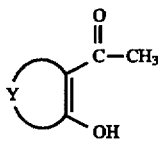

wherein

is as defined above, with a compound represented by the following general formula (II)

wherein

is as defined above.

2. A process for preparing a spiropyrone compound according to claim 1, wherein

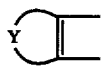

is a divalent aromatic hydrocarbon group or a divalent unsaturated heterocyclic group which may be substituted with at least one member selected from the group consisting of a halogen atom, a hydroxyl group, a cyano group, a nitro group, an alkyl group having 1 to 4 carbon atoms, an alkoxy group having 1 to 4 carbon atoms, an aryl group having 6 to 10 carbon atoms, an an alkylamino group having 1 to 4 carbon atoms, a dialkylamino group having 2 to 8 carbon atoms, a halogenoalkyl group having 1 to 2 carbon atoms, and 5-membered and 6-membered monocyclic heterocyclic groups having one or two sulfur, oxygen or nitrogen atoms.

3. A process for preparing a spiropyrone compound according to claim 1, wherein

is a divalent aromatic hydrocarbon group or a divalent unsaturated heterocyclic group which may be substituted with 1 to 3 members which can be the same or different, said 1 to 3 members being selected from the group consisting of a halogen atom, a hydroxyl group, a cyano group, a nitro group, an alkyl group having 1 to 4 carbon atoms, an alkoxy group having 1 to 4 carbon atoms, an aryl group having 6 to 10 carbon atoms, an alkylamino group having 1 to 4 carbon atoms, a dialkylamino group having 2 to 8 carbon atoms, a halogenoalkyl group having 1 to 2 carbon atoms, and 5-membered and 6-membered monocyclic heterocyclic groups having one or two sulfur, oxygen or nitrogen atoms.

4. A process for preparing a spiropyrone compound according to claim 1, therein the divalent aromatic hydrocarbon group is a divalent group derived from one benzene ring or a fused ring comprising 2 to 4 benzene rings.

5. A process for preparing a spiropyrone compound according to claim 1, wherein the divalent unsaturated heterocyclic group is a divalent group derived from a 5- or 6-membered monocyclic heterocyclic ring containing one or two sulfur, oxygen or nitrogen atoms, or a fused heterocyclic ring formed by fusion of a benzene ring to said monocyclic heterocyclic ring.

6. A process for preparing a spiropyrone compound according to claim 1, wherein the divalent aromatic hydrocarbon group is a divalent group derived from a benzene ring, a naphthalene ring or a phenanthrene ring.

7. A process for preparing, a spiropyrone compound according to claim 1, wherein the unsaturated heterocyclic group is a divalent group derived from a pyridine ring a quinoline ring, a pyrrole ring, a furan ring, a benzofuran ring, a thiophone ring or a benzothiophene ring.

8. A process for preparing a spiropyrone compound according to claim 1, wherein

is a bicyclo(3,3,1)9-nonenylidene group which may be substituted with at least one member selected from the group consisting of a halogen atom, a hydroxyl group, a cyano group, a nitro group, a carboxyl group, an alkyl group having 1 to 4 carbon atoms, an alkoxy group having 1 to 4 carbon atoms, a halogenoalkyl group having 1 to 2 carbon atoms, an aryl group having 6 to 10 carbon atoms, an aryloxy group having 6 to 10 carbon atoms, an aralkyl group having 7 to 10 carbon atoms, an aralkoxy group having 7 to 10 carbon atoms an alkylamino group having 1 to 4 carbon atoms, a dialkylamino group having 2 to 8 carbon atoms and an alkoxycarbonyl group having 2 to 10 carbon atoms.

9. A process for preparing a spiropyrone compound according to claim 1, wherein the primary or secondary amine are represented by the formula

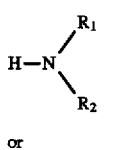

where either one of the groups $R_1$ and $R_2$ is a hydrogen atom and the other one is an alkyl group, or both of them are the same or different alkyl groups; and $R_3$ is an alkylene group having 3 to 6 carbon atoms, an oxyalkylene group having 3 to 6 carbon atom, a thioalkylene group having 3 to 6 carbon atoms, or an azoalkylene group having 3 to 6 carbon atoms.

10. A process for preparing a spiropyran compound represented by the following formula wherein is a substituted or an unsubstituted aromatic hydrocarbon group or a substituted or an unsubstituted unsaturated heterocyclic group, and is a substituted or an unsubstituted 2-bicyclo[3,3,1]9-nonenylidene group, comprising reducing a compound represented by the following general formula wherein are as defined above and dehydrating the obtained compound represented by the following general formula 11. A process for preparing a spiropyran compound represented by the following formula wherein is a substituted or an unsubstituted aromatic hydrocarbon group or a substituted or an unsubstituted unsaturated heterocyclic group, and is a substituted or an unsubstituted 2-bicyclo[3,3,1]9-nonenylidene group, and $R_4$ is an alkyl group, an aralkyl group or an aryl group, comprising reacting a compound represented by the following general formula wherein are as defined above, with a compound of the formula $R_4$—MgX or $R_4$—Li wherein $R_4$ is an alkyl group, an aryl group or an aralkyl group, and X is a halogen atom, and dehydrating the obtained compound represented by the following general formula

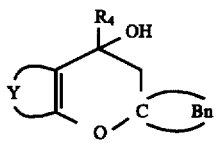

wherein

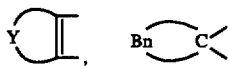

and are as defined above.

12. A process for preparing a spiropyran compound represented by the following formula

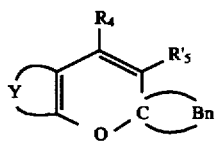

wherein

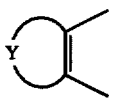

is a substituted or an unsubstituted aromatic hydrocarbon group or a substituted or an unsubstituted unsaturated heterocyclic group,

is a substituted or an unsubstituted 2-bicyclo[3,3,1]9-nonenylidene group, and either one of $R_4$ and $R'_5$ is a hydrogen atom and the other one is a group R, comprising reacting a compound represented by the following general formula

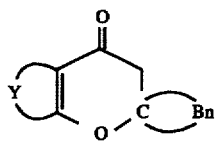

wherein

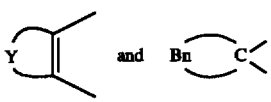

are as defined above, with an amine of the formula

R—H wherein R is a substituted amino group.

13. A process for preparing a spiropyran compound represented by the following formula

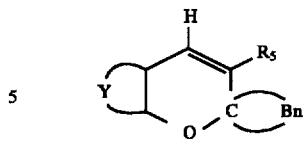

wherein

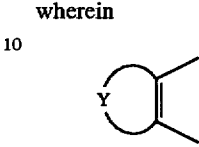

is a substituted or an unsubstituted aromatic hydrocarbon group or a substituted or an unsubstituted unsaturated heterocyclic group,

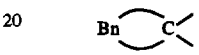

is a substituted or an unsubstituted 2-bicyclo[3,3,1]9-nonenylidene group, and $R_5$ is an alkyl group, an aryl group or an aralkyl group, comprising reacting a compound represented by the following general formula

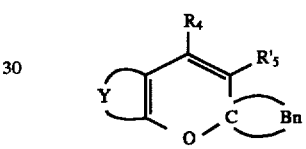

wherein

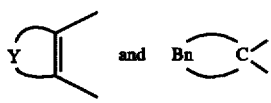

are as defined above, either one of $R_4$ or $R'_5$ is a hydrogen atom and the other one is a substituted amino group, with a compound of the formula

$R_5X$ wherein $R_5$ is as defined above, and reducing and dehydrating the obtained compound represented by the following general formula

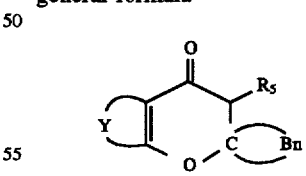

wherein

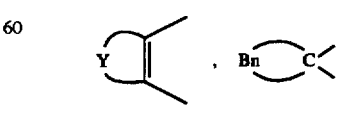

and $R_5$ are as defined above.

14. A process for preparing a spiropyran compound represented by the following formula

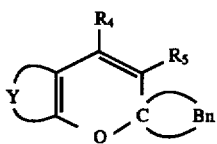

wherein

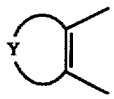

is a substituted or an unsubstituted aromatic hydrocarbon group or a substituted or an unsubstituted unsaturated heterocyclic group,

is a substituted or an unsubstituted 2-bicyclo[3,3,1]9-nonenylidene group, $R_4$ is an alkyl group an aryl group or an aralkyl group, and $R_5$ is an alkyl group, an aryl group or an aralkyl group comprising reacting a compound represented by the following general formula

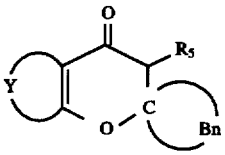

wherein

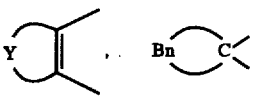

and $R_5$ are as defined above, with a compound of the formula $R_4$—MgX or $R_4$—Li wherein $R_4$ is as defined above, and X is halogen and dehydrating the obtained compound represented by the following formula

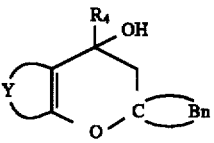

wherein $R_4$ and $R_5$ are as defined above.

15. A spiropyran compound represented by the following general formula

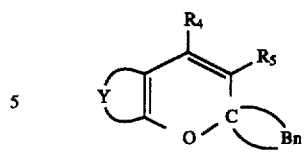

wherein

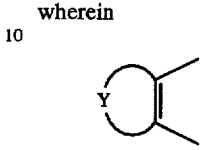

is a substituted or an unsubstituted aromatic hydrocarbon group or a substituted or an unsubstituted unsaturated heterocyclic group,

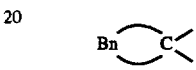

is a substituted or an unsubstituted 2-bicyclo[3,3,1]9-nonenylidene group, $R_4$ $R_5$ are the same or different and are independently a hydrogen atoms, alkyl groups, aryl groups, aralkyl groups or substituted amino groups, respectively, and when either one of R4 and R5 is a substituted amino group, the other one is a hydrogen atom.

16. A process for preparing a spiropyrone compound according to claim 8, wherein

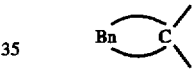

contains 1 to 3 of said members.

17. A process for preparing a spiropyran compound represented by the following formula (VI)

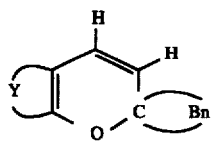

(VI)

comprising preparing a spiropyrone compound represented by the following formula (III)

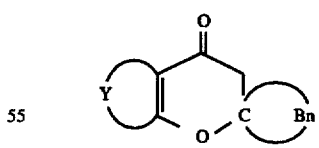

(III)

wherein

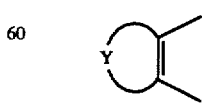

is a substituted or an unsubstituted aromatic hydrocarbon group or a substituted or an unsubstituted unsaturated heterocyclic group, and

is a substituted or an unsubstituted 2-bicyclo[3,3,1]9-nonenylidene group, by reacting in the presence of a primary or secondary amine condensing agent a compound represented by the following formula (I)

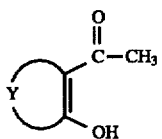

(I)

wherein

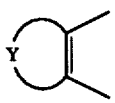

is as defined above, with a compound represented by the following formula (II)

(II)

wherein

is as defined above, and reducing the resulting spiropyrone to prepare a compound represented by the following formula (A)

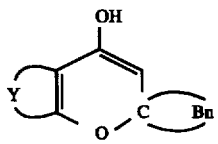

(A)

and dehydrating the compound of formula (A) to obtain the compound of formula (VI).

18. A process for preparing a spiropyran compound represented by the following formula (VII)

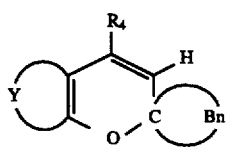

(VII)

wherein

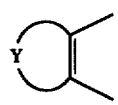

is a substituted or an unsubstituted aromatic hydrocarbon group or a substituted or an unsubstituted unsaturated heterocyclic group, and

is a substituted or an unsubstituted 2-bicyclo[3,3,1]9-nonenylidene group, and $R_4$ is an alkyl group, an aralkyl group or an aryl group, comprising preparing a spiropyrone compound represented by the following formula (III)

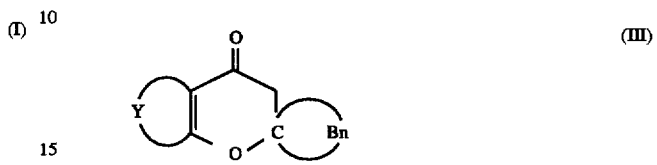

(III)

wherein

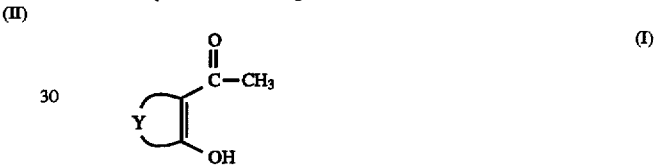

are as defined above, by reacting in the presence of a primary or secondary amine condensing agent a compound represented by the following formula (I)

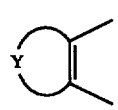

(I)

wherein

is as defined, above with a compound represented by the following formula (II)

(II)

Bn⌒C=O wherein

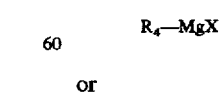

is as defined above, and reacting the obtained spiropyrone with a compound of the formula $R_4$—MgX or $R_4$—Li wherein $R_4$ is defined above and X is a halogen atom, to obtain a compound represented by formula (B)

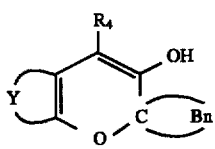

wherein

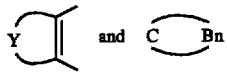

and $R_4$ are as defined above and dehydrating the compound of formula (B) to obtain the compound of formula (VII).

19. The process for preparing a spiropyran compound represented by the following formula (V)

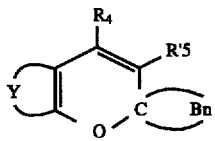

(V)

wherein

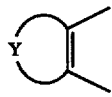

is a substituted or an unsubstituted aromatic hydrocarbon group or a substituted or an unsubstituted unsaturated heterocyclic group,

is a substituted or an unsubstituted 2-bicyclo[3,3,1]9-nonenylidene group, and either one of $R_4$ and $R'_5$ is a hydrogen atom and the other one is a group R, comprising preparing a spiropyrone compound represented by the following formula (III)

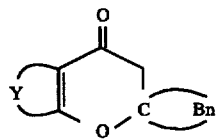

where

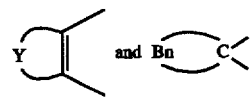

are as defined above, by reacting in the presence of a primary or secondary amine condensing agent a compound represented by the following formula (I)

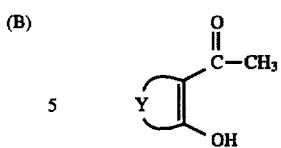

(B)

wherein

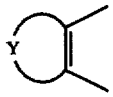

is as defined above, with a compound represented by the following formula (II)

(II)

wherein

is as defined above, and reacting the obtained spiropyrone with an amine of the formula

R—H wherein R is a substituted amino group to obtain the compound of formula (V).

20. A process for preparing a spiropyran compound represented by the following formula (VIII)

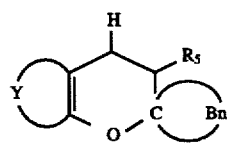

(VIII)

wherein

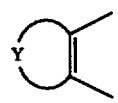

is a substituted or an unsubstituted aromatic hydrocarbon groupo or a substituted or an unsubstituted unsaturated heterocyclic group

is a substituted or an unsubstituted 2-bicyclo (3,3,1) 9-nonenylidene group, and $R_5$ is an alkyl group, an aryl group or an aralkyl group, comprising reacting a compound of the formula (III)

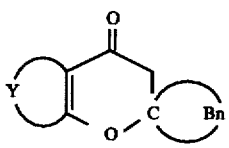

wherein

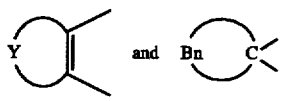

are as defined above, with an amine of the formula R-H, wherein R is a substituted amimo group, to form a compound of the following formula (V)

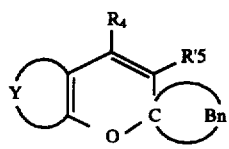

(V)

wherein

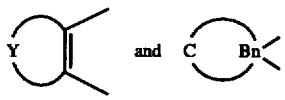

are as defined above, either one of $R_4$ and $R_5$ is a hydrogen atom and the other one is a group R, reacting the compound of formula (V) with a compound of the formula $R_5X$ wherein $R_5$ is defined above and X is a halogen atom, and reducing and dehydrating the obtained spiropyrone compound represented by the following formula (IX)

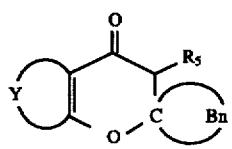

(IX)

wherein

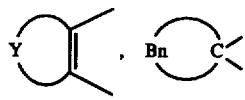

and $R_5$ are as defined above to produce the compound of formula (VIII).

21. A process for preparing a spiropyran compound represented by the following formula (IV)

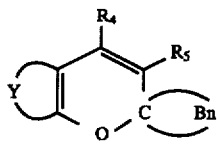

(IV)

wherein

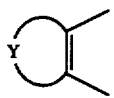

(III)

is a substituted or an unsubstituted aromatic hydrocarbon group or a substituted or an unsubstituted unsaturated heterocyclic group,

is a substituted or an unsubstituted 2-bicylo[3,3,1]9-nonenylidene group, $R_4$ is an alkyl group, an aryl group or an aralkyl group, and $R'_5$ is an alkyl group, an aryl group or an aralkyl group, comprising preparing a spiropyrone by reacting a compound of the formula (III)

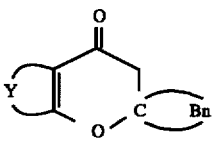

(III)

wherein

are as defined above, with an amine of the formula R—H, wherein R is a substituted amino group to form a compound of the following formula (V)

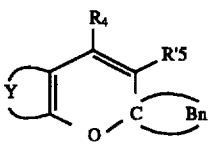

(V)

wherein

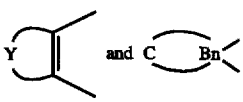

are defined above, either one of $R_4$ and $R_5$ is a hydrogen atom and the other one is group R, reacting the obtained compound with a compound of the formula $R_5X$ wherein $R_5$ is defined above to provide a spiropyrone compound of the following formula (IX)

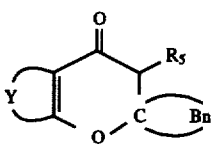

(IX)

wherein

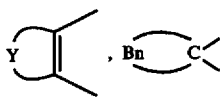

and $R_5$ are defined above and reacting the spiropyrone of formula (IX) with a compound of the formula

or

wherein $R_4$ is defined above and X is a halogen atom, to obtain a compound of formula (B)

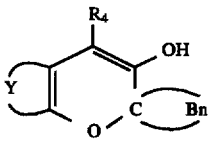
(B)

wherein

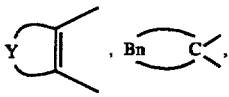

$R_4$ are as defined above and dehydrating the compound of formula (B) to obtain the compound of formula (IV).

22. The process of claim 12 wherein the substituted amino group is a primary or secondary amine selected from the group consisting of compounds of the formula

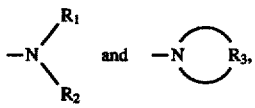

wherein $R_1$ and $R_2$ are each, independently, the same or different alkyl groups having 1 to 6 carbon atoms or one of $R_1$ or $R_2$ is a hydrogen atom and the other is an alkyl group having 1 to 6 carbon atoms, and $R_3$ is an alkylene group having 3 to 6 carbon atoms.

23. The process of claim 20 wherein the substituted amino group is a primary or secondary amine selected from the group consisting of compounds of the formula

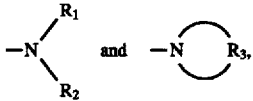

wherein $R_1$ and $R_2$ are each, independently, the same or different alkyl groups having 1 to 6 carbon atoms or one of $R_1$ and $R_2$ is a hydrogen atom and the other is an alkyl group having 1 to 6 carbons atoms, and $R_3$ is an alkylene group having 3 to 6 carbon atoms.

24. The process of claim 21 wherein the substituted amino group is a primary or secondary amine selected from the group consisting of compounds of the formula

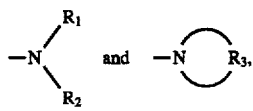

wherein $R_1$ and $R_2$ are each, independently, the same or different alkyl groups having 1 to 6 carbon atoms or one of $R^1$ and $R_2$ is a hydrogen atom and the other is an alkyl group having 1 to 6 carbon atoms, and $R_3$ is an alkylene group having 3 to 6 carbon atoms.

25. The process of claim 1 wherein the condensing agent is diethylamine, a pyrrolidine, a piperidine or a morpholine.

26. The process of claim 1 wherein the condensing agent is present in an amount of from 0.1 to 10 moles per mole of the compound represented by the general formula (I).

27. A process of using a ketone of formula (II)

(II)

wherein said ketone is a substituted or an unsubstituted 2-bicyclo[3.3.1]9-nonenylidene group, to form a spiropyrone compound represented by the following formula (III)

(III)

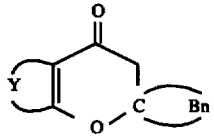

wherein

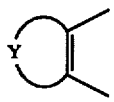

is a substituted or an unsubstituted aromatic hydrocarbon group or a substituted or an unsubstituted saturated heterocyclic group and

is as defined above, which comprises reacting said ketone in the presence of a primary or secondary amine condensing agent with a compound of the following formula (I)

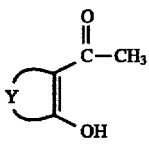

wherein

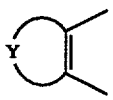

is as defined above, to obtain said spiropyrone, wherein the ketone and the compound of formula (I) are mixed at a molar ratio of from 1:10 to 10:1, to thereby obtain a yield of from about 69% to about 81% spiropyrone of the formula (III).

28. A process of using a ketone of formula (II)

  (II)

wherein said ketone is a substituted or an unsubstituted 2-bicyclo[3.3.1]9-nonenylidene group, to form a spiropyran compound represented by the following formula (VI)

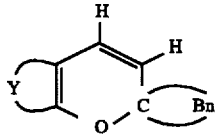  (VI)

wherein

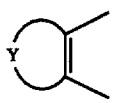

is a substituted or an unsubstituted aromatic hydrocarbon group or a substituted or an unsubstituted unsaturated heterocyclic group,

is a substituted or an unsubstituted 2-bicyclo[3.3.1]9-nonenylidene group, comprising forming a spiropyrone compound represented by the following formula (III)

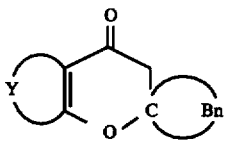  (III)

wherein

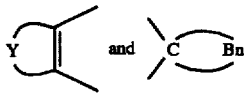

are as defined above, by reacting said ketone in the presence of a primary or secondary amine condensing agent with a compound of the following formula (I)

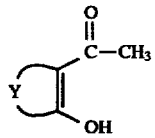  (I)

wherein

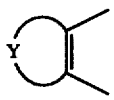

is as defined above to form a spiropyrone compound of formula (III) and reducing the spiropyrone of formula (III) to prepare a compound represented by the formula (A)

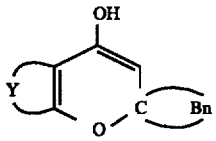  (A)

and dehydrating the compound of formula (A) to obtain the compound of formula (VI).

29. A process for preparing a spiropyrone compound according to claim 1, which comprises reacting the compound of formula (I) with the compound of formula (II) at a molar ratio of from 1:10 to 10:1, at a reaction temperature of from 0° to 200° C., for from 1 to 20 hours.

30. A process for preparing a spiropyrone compound according to claim 29, wherein the reaction between the compound of formula (I) and the compound of formula (II) is carried out in a polar non-protonic solvent in the presence of said condensing agent which is a primary or secondary amine represented by the formula $$H-N\begin{matrix}R_1\\R_2\end{matrix}$$

or $$H-N\underset{\smile}{\phantom{X}}R_3$$

where either one of the groups $R_1$ and $R_2$ is a hydrogen atom and the other one is an alkyl group, or both of them are the same or different alkyl groups; and $R_3$ is an alkylene group having 3 to 6 carbon atoms, an oxyalkylene group having 3 to 6 carbon atoms, a thioalkylene group having 3 to 6 carbon atoms, or an azoalkylene group having 3 to 6 carbon atoms.

31. A process for preparing a spiropyrone compound according to claim 30 which further comprises removing water formed during the reaction between the compound of formula (I) and the compound of formula (II).

32. A process for preparing a spiropyrone compound according to claim 31 wherein the yield of the spiropyrone compound of the formula (III) after reaction for up to about 10 hours is in the range from about 69% to about 85%.

* * * * *